(12) United States Patent
Yamada

(10) Patent No.: US 7,637,615 B2
(45) Date of Patent: Dec. 29, 2009

(54) DEVICE FOR TRACKING PUPIL OF EYEBALL USING INTENSITY CHANGES OF REFLECTED LIGHT FROM EYEBALL AND IMAGE DISPLAY USING THE SAME

(75) Inventor: Shoji Yamada, Konan (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 233 days.

(21) Appl. No.: 11/705,471

(22) Filed: Feb. 13, 2007

(65) Prior Publication Data

US 2007/0159599 A1   Jul. 12, 2007

Related U.S. Application Data

(63) Continuation-in-part of application No. PCT/JP2005/014719, filed on Aug. 11, 2005.

(30) Foreign Application Priority Data

Aug. 19, 2004   (JP) ............... 2004-238994

(51) Int. Cl.
*A61B 3/10* (2006.01)
(52) U.S. Cl. ..................... 351/205; 351/209
(58) Field of Classification Search ........ 351/205, 351/209
See application file for complete search history.

(56) References Cited

U.S. PATENT DOCUMENTS

| 5,467,104 | A | 11/1995 | Furness, III et al. |
| 5,596,339 | A | 1/1997 | Furness, III et al. |
| 5,659,327 | A | 8/1997 | Furness, III et al. |
| 6,008,781 | A | 12/1999 | Furness, III et al. |
| 6,317,103 | B1 | 11/2001 | Furness, III et al. |
| 6,639,570 | B2 | 10/2003 | Furness, III et al. |
| 7,374,287 | B2 * | 5/2008 | Van de Velde ............... 351/221 |
| 2002/0163484 | A1 | 11/2002 | Furness, III et al. |
| 2003/0095081 | A1 | 5/2003 | Furness, III et al. |
| 2004/0109135 | A1 | 6/2004 | Watanabe et al. |

FOREIGN PATENT DOCUMENTS

| JP | A H08-502372 | 3/1996 |
| JP | A H08-205052 | 8/1996 |
| JP | A H08-206079 | 8/1996 |
| JP | B 3435160 | 5/2003 |
| JP | A 2004-191962 | 7/2004 |

* cited by examiner

*Primary Examiner*—Jordan M. Schwartz
*Assistant Examiner*—James C Jones
(74) *Attorney, Agent, or Firm*—Oliff & Berridge, PLC

(57) ABSTRACT

A technique is disclosed of tracking a position of a pupil of a viewer's eyeball, by directing light toward the eyeball and using a portion of the light reflected from the eyeball. In the technique, the detection is performed of the intensity of a reflected light beam which is a portion of a light beam entering the eyeball which is reflected therefrom. An intensity signal indicative of the intensity of the reflected light beam is produced. The pupil position is tracked based on intensity changes of the reflected light beam represented by the intensity signal.

22 Claims, 12 Drawing Sheets

DEVICE FOR TRACKING PUPIL OF EYEBALL USING INTENSITY CHANGES OF REFLECTED LIGHT FROM EYEBALL AND IMAGE DISPLAY USING THE SAME

CROSS-REFERENCE TO RELATED APPLICATIONS

This application is based on Japanese Patent Application No. 2004-238994 filed Aug. 19, 2004, and International Application No. PCT/JP2005/014719 filed Aug. 11, 2005, the contents of which are incorporated hereinto by reference.

This application is a continuation-in-part application of International Application No. PCT/JP2005/014719 filed Aug. 11, 2005, now pending, which was published in Japanese under PCT Article 21(2).

BACKGROUND OF THE INVENTION

1. Field of the Invention

The invention relates to techniques of tracking the position of a pupil of an eyeball, by directing light toward the eyeball and using a portion of the light reflected from the eyeball.

2. Description of the Related Art

Techniques have been in existence which are capable of tracking or monitoring the position of a pupil of an eyeball, by directing light toward the eyeball and using a portion of the light reflected from the eyeball.

Japanese Patent No. 3435160 discloses two exemplary conventional approaches of such techniques. These exemplary conventional approaches are in common in that a technique of tracking a pupil position is implemented together with an image display technique in which a desired image is projected directly onto a viewer's retina, by causing imaging light for displaying the image, to enter the retina through a viewer's pupil.

More specifically, in the first one of those two exemplary conventional approaches, display-purpose raster light is thrown toward an eyeball, and a portion of the raster light reflected from the surface of the eyeball is directed by a lens toward a position-sensing diode for light collection. The position-sensing diode is electrically coupled to an eye tracker for tracking or detecting a pupil position. Thus, in this exemplary conventional approach, the pupil position is tracked using imaging light originally produced for displaying a desired image.

In the second one of those two exemplary conventional approaches, there is an eye tracker including an infrared-light source. The infrared-light source illuminates an eyeball surface directly or indirectly with lower-luminance infrared light exclusively for the purpose of tracking of the pupil position.

In this approach, the eyeball surface is identified as a two-dimensional image through an optical combiner, a lens, and a Charge Coupled Device (CCD) sensor. The CCD sensor is formed as a two-dimensional array of a number of light-reception elements which create a two-dimensional array of a number of pixels.

Further, in this approach, an output signal of the CCD sensor is processed by a pupil position processor. More specifically, the pupil position processor performs image processing for the output signal of the CCD sensor, to thereby track a pupil position. The image processing is performed in a manner that a center position of the pupil is determined based on the center or the outline of an image of the eyeball captured by the CCD sensor.

Still further, in this approach, the infrared light is directed to the eyeball along an optical path separate from that along which imaging light enters the pupil, wherein the imaging light is originally produced for displaying a desired image.

BRIEF SUMMARY OF THE INVENTION

In the aforementioned first exemplary conventional approach, however, reference light (i.e., tracking light) to be referenced for tracking or detection of a pupil position is a portion of the imaging light reflected from an eyeball surface, with the result that, as the luminance of the imaging light changes, the luminance of the reference light changes.

For this reason, this exemplary conventional approach is likely to cause a problem that a reduction in luminance of the imaging light leads to an undesirable reduction in tracking accuracy of a pupil position due to a shortage of an amount of the reference light, resulting from unavoidable dependency of the tracking accuracy of a pupil position upon the luminance of the reference light.

In contrast, in the aforementioned second exemplary conventional approach, tracking or detection of a pupil position requires the pupil position processor to perform the image processing based on the output signal of the CCD sensor.

For this reason, this exemplary conventional approach is likely to cause a problem that the manufacturing cost increases, resulting from the requirement of the pupil position processor to achieve a high-speed image processing ability.

It is therefore an object of the present invention to improve the technique of tracking the position of a pupil of an eyeball, by directing light toward the eyeball and using a portion of the light reflected from the eyeball.

According to a first aspect of the invention, a device for tracking a position of a pupil of an eyeball, by directing light toward the eyeball and using a portion of the light which is reflected from the eyeball is provided.

This device comprises:

a light emitter emitting a light beam;

a scanner scanning two-dimensionally the light beam emitted from the light emitter, over the eyeball, in a primary scan direction and a secondary scan direction which are oriented crosswise relative to each other, along a plurality of successive scan lines;

a detector detecting a time-varying intensity of a reflected light beam which is a portion of the light beam entering a surface of the eyeball which is reflected therefrom, and producing an intensity signal indicative of the intensity of the reflected light beam; and a processor which tracks a pupil position based on intensity changes of the reflected light beam represented by the intensity signal outputted from the detector.

According to a second aspect of the invention, an apparatus for projecting an image directly onto a retina of a viewer, by directing a visible light beam representing the image toward the retina through a pupil of the viewer is provided.

This apparatus comprises:

a display-purpose light emitter emitting the visible light beam for displaying the image;

a tracking-purpose light emitter emitting a non-visible light beam toward an eyeball of the viewer, for tracking a pupil position;

a combiner combining the visible light beam emitted from the display-purpose light emitter and the non-visible light beam emitted from the tracking-purpose light emitter with each other, to thereby produce a composite light beam;

a scanner scanning the produced composite light beam two-dimensionally, over the eyeball, in a primary scan direction and a secondary scan direction which are oriented crosswise relative to each other, along a plurality of successive scan lines;

a guide guiding the scanned composite light beam toward the pupil;

a detector detecting a time-varying intensity of a reflected light beam which is a portion of the non-visible light beam entering a surface of the eyeball which is reflected therefrom, and producing an intensity signal indicative of the intensity of the reflected light beam; and a controller which tracks the pupil position based on intensity changes of the reflected light beam represented by the intensity signal outputted from the detector, and which controls an optical axis along which the visible light beam travels toward the eyeball, so as to follow an actual pupil position, based on the tracked pupil position.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
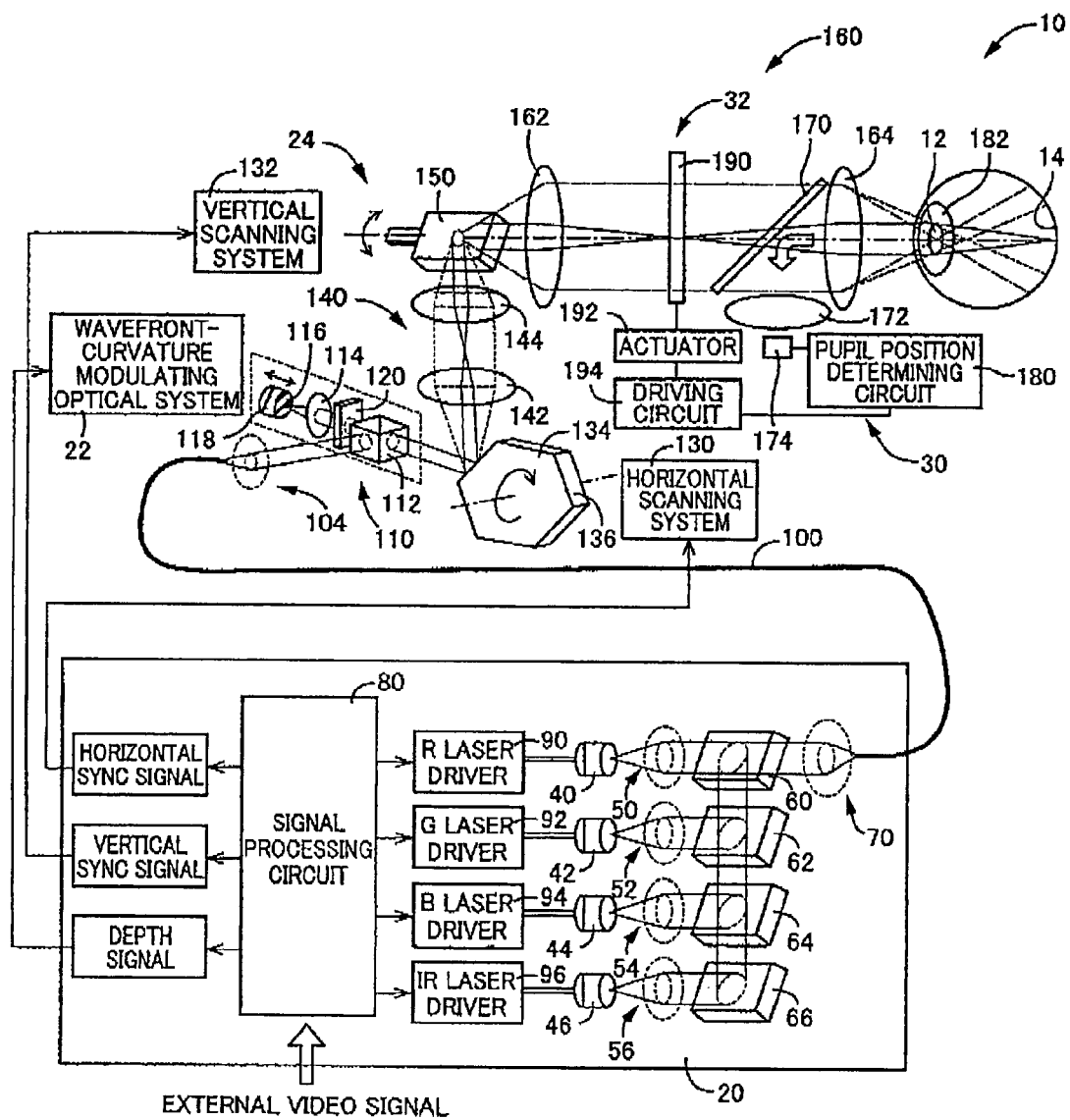
FIG. 1 is a schematic view illustrating a retinal scanning display constructed according to a first embodiment of the present invention.

The Object mentioned above may be achieved according to any one of the following modes of this invention.

These modes will be stated below so as to be sectioned and numbered, and so as to depend upon the other mode or modes, where appropriate This is for a better understanding of some of a plurality of technological features and a plurality of combinations thereof disclosed in this description, and does not mean that the scope of these features and combinations is interpreted to be limited to the scope of the following modes of this invention.

That is to say, it should be interpreted that it is allowable to select the technological features which are stated in this description but which are not stated in the following modes, as the technological features of this invention.

Furthermore, stating each one of the modes of the invention in such a dependent form as to depend from the other mode or modes does not exclude the possibility that the technological features set forth in a dependent-form mode become independent of those set forth in the corresponding depended mode or modes and to be removed therefrom. It should be interpreted that the technological features set forth in a dependent-form mode are allowed to become independent, where appropriate.

(1) A device for tracking a position of a pupil of an eyeball, by directing light toward the eyeball and using a portion of the light which is reflected from the eyeball, the device comprising:

a light emitter emitting a light beam;

a scanner scanning two-dimensionally the light beam emitted from the light emitter, over the eyeball, in a primary scan direction and a secondary scan direction which are oriented crosswise relative to each other, along a plurality of successive scan lines;

a detector detecting a time-varying intensity of a reflected light beam which is a portion of the light beam entering a surface of the eyeball which is reflected therefrom, and producing an intensity signal indicative of the intensity of the reflected light beam; and a processor which tracks a pupil position based on intensity changes of the reflected light beam represented by the intensity signal outputted from the detector.

The present inventor has found that, during a two-dimensional scan of a light beam over an eyeball surface in a principal scan direction and a secondary scan direction which are oriented crosswise relative to each other, the intensity of a portion of the light beam reflected from the eyeball surface changes over time, as the light beam moves or changes spatially over the eyeball surface.

Further, the present inventor has also found that there exists a preserved dependency between actual profiles or patterns of intensity changes of the reflected light beam from the eyeball surface and actual pupil positions.

Based on the above findings, this device constructed according to the present mode is configured such that a detector detects a time-varying intensity of a portion of the light beam reflected from the eyeball, as an intensity of a reflected light beam, and outputs an intensity signal indicative of the detected intensity of the reflected light beam.

Further, this device is also configured such that a processor detects or tracks a pupil position based on the intensity changes of the reflected light beam represented by the intensity signal outputted from the detector.

This device, therefore, would allow a pupil position to be tracked without requiring complicated image-processing for a signal outputted from the detector.

Further, this device would also allow the detector not to require the capability of detecting or sensing a two-dimensional position at which a reflected light beam from the eyeball surface has impinged on a relatively large two-dimensional light-entrance area, but to at least require the capability of detecting or sensing the intensity of a reflected light beam from the eyeball surface which has impinged on a relatively small light-entrance area.

This device, as a result, would facilitate a reduction in size and cost of the detector.

An exemplary configuration of the "detector" set forth in the present mode may include an optical collector (e.g., a convex lens) collecting a reflected light beam from an eyeball surface, and a sensor (e.g., a photodiode) receiving the collected reflected light beam and producing a signal indicative of the intensity of the received reflected light beam in a binary or multi-level signal format.

The "light beam" set forth in the present mode, when there is the need to track a pupil position unnoticeably, is preferably a non-visible light beam. However, the "light beam," in the absence of such a need, may be a visible light beam.

(2) The device according to mode (1), wherein the intensity of the reflected light beam represented by the intensity signal outputted from the detector has first intensity changes dependent on position changes of the light beam along the individual scan lines, and second intensity changes dependent on position changes of the light beam across the scan lines, and the processor tracks a two-dimensional pupil position based on the first and second intensity changes of the reflected light beam.

The present inventor has found that, during a two-dimensional scan of a light beam over an eyeball surface in a principal scan direction and a secondary scan direction which are crosswise relative to each other, the intensity of a portion of the light beam reflected from the eyeball surface changes, as the light beam moves along the individual scan lines, and as the light beam moves across the scan lines.

Further, the present inventor has also found that there exists a preserved dependency between actual profiles or patterns of intensity changes of the reflected light beam from the eyeball surface and actual pupil positions.

Based on the above findings, this device constructed according to the present mode is configured such that a two-dimensional position of the pupil is determined or tracked based on first intensity changes in the intensity of the reflected light beam represented by the intensity signal outputted from the detector, which are dependent on position changes of the light beam along the individual scan lines, and second intensity changes in the intensity of the reflected light beam, which are dependent on position changes of the light beam across the scan lines.

(3) The device according to mode (1) or (2), wherein the light beam is scanned two-dimensionally on a scan region which is located on the surface of the eyeball so as to cover the pupil with an area size larger than that of the pupil.

Reflective indexes of an eyeball surface are distributed not uniformly but variously in a manner that, for example, the reflective indexes are higher at an iris, which surrounds a pupil, than at the remaining areas.

For this reason, for a pupil position to be accurately tracked by deploying such a distribution pattern of the reflective indexes of the eyeball surface, a light beam to be caused to enter the eyeball is preferably scanned two-dimensionally on a scan region located on the eyeball surface so as to cover the pupil with an area size larger than that of the pupil.

Based on the above findings, this device according to the present mode has been created.

(4) The device according to mode (3), wherein the scanner scans the light beam entering the scanner, to thereby emit scanning light, and the emitted scanning light enters the eyeball so as to have a focus position which is located on an optical axis extending between the scanner and a retina of the eyeball, at a predetermined distance from the pupil.

In this device, a cross section of the scanning light taken at the same position as that of the eyeball surface corresponds to a two-dimensional scan region formed on the eyeball surface in connection with the scanning light. The scan region enlarges as the cross section enlarges.

On the other hand, the cross section is larger when the scanning light is focused at a position spaced apart by a predetermined distance from the pupil along an optical axis between the scanner and the pupil, than when the scanning light is focused exactly at the position of the pupil.

This device according to the present mode, therefore, would allow a scan region on which an eyeball surface is scanned two-dimensionally with a light beam to be prepared so as to cover the pupil with an area size larger than that of the pupil.

(5) The device according to any one of modes (1)-(4), wherein the processor, in a presence of two high-level portions of the intensity signal, tracks the pupil position based on the two high-level portions, per scan line, and each one of the high-level portions of the intensity signal indicates that the intensity of the reflected light beam exceeds a threshold value.

When a scan region is located on an eyeball surface so as to cover a pupil with an area size larger than that of the pupil, each scan line on the eyeball surface runs across both the pupil and an iris surrounding the pupil.

In addition, when the eyeball surface is viewed along each scan line, there are two portions of the iris located on both sides of the pupil, wherein each of the two portions has a higher reflective index than that of the pupil.

As a result, when the eyeball surface is scanned such that a light beam runs on the eyeball surface so as to pass through a pupil surface along the individual scan lines, the detector produces an intensity signal in a waveform showing two high-level portions each indicative of a higher intensity of the reflected light beam from the eyeball surface than those in adjacent areas, with a low-level portion indicative of a lower intensity of the reflected light beam being interposed between the two high-level portions.

The middle position between those two high-level portions of the produced intensity signal represents the center position of the pupil as viewed in parallel to the scan lines.

In addition, the position of one of the scan lines, the intensity signal of which has its two high-level portions spaced apart from each other by a substantially maximum distance represents the center position of the pupil as viewed across the scan lines.

Based on the above findings, in this device constructed according to the present mode, the pupil position is tracked, per scan line, based on two high-level portions of the intensity signal, if any, wherein each high-level portion indicates that the intensity of the reflected light beam exceeds a threshold value.

(6) The device according to mode (5), wherein the processor includes a first position tracker tracking the pupil position in the primary scan direction, based on a middle position between the two high-level portions of the intensity signal.

As described above the middle position between two high-level portions of an intensity signal outputted from the detector represents the center position of the pupil as viewed in parallel to the scan lines.

Based on the above findings, in this device constructed according to the present mode, the pupil position is tracked in the primary scan direction, based on a middle position between the two high-level portions of the intensity signal outputted from the detector.

(7) The device according to mode (5) or (6), wherein the processor includes a second position tracker tracking the pupil position in the secondary scan direction, based on a position of one of the plurality of scan lines, the intensity signal of which has the two high-level portions spaced apart from each other by a substantially maximum distance.

As described above, the position of one of the scan lines, the intensity signal of which has its two high-level portions spaced apart from each other by a substantially maximum distance represents the center position of the pupil as viewed across the scan lines.

Based on the above findings, in this device constructed according to the present mode, the pupil position is tracked in the secondary scan direction, based on the position of one of the scan lines, the intensity signal of which has its two high-level portions spaced apart from each other by a substantially maximum distance.

(8) An apparatus for projecting an image directly onto a retina of a viewer, by directing a visible light beam representing the image toward the retina through a pupil of the viewer, the apparatus comprising:

a display-purpose light emitter emitting the visible light beam for displaying the image;

a tracking-purpose light emitter emitting a non-visible light beam toward an eyeball of the viewer, for tracking a pupil position;

a combiner combining the visible light beam emitted from the display-purpose light emitter and the non-visible light beam emitted from the tracking-purpose light emitter with each other, to thereby produce a composite light beam;

a scanner scanning the produced composite light beam two-dimensionally, over the eyeball, in a primary scan direction and a secondary scan direction which are oriented crosswise relative to each other, along a plurality of successive scan lines;

a guide guiding the scanned composite light beam toward the pupil;

a detector detecting a time-varying intensity of a reflected light beam which is a portion of the non-visible light beam entering a surface of the eyeball which is reflected therefrom, and producing an intensity signal indicative of the intensity of the reflected light beam; and a controller which tracks the pupil position based on intensity changes of the reflected light beam represented by the intensity signal outputted from the detector, and which controls an optical axis along which the visible light beam travels toward the eyeball, so as to follow an actual pupil position, based on the tracked pupil position.

Similarly with the device constructed according to the previous mode (1), this apparatus constructed according to the present mode is configured such that a detector detects the intensity of a portion of the light beam reflected from the eyeball, as an intensity of a reflected light beam, and produces an intensity signal indicative of the detected intensity of the reflected light beam.

Similarly with the device according to mode (1), this apparatus is also configured such that a controller determines or tracks a pupil position based on the intensity changes of the reflected light beam represented by the intensity signal outputted from the detector.

This apparatus, therefore, would allow a pupil position to be tracked without requiring complicated image-processing for a signal outputted from the detector.

Further, this apparatus would also allow the detector not to require the capability of detecting or sensing a two-dimensional position at which a reflected light beam from the eyeball surface has impinged on a relatively large two-dimensional light-entrance area, but to at least require the capability of detecting or sensing the intensity of a reflected light beam from the eyeball surface which has impinged on a relatively small light-entrance area.

This apparatus, as a result, would facilitate a reduction in size and cost of the detector.

This apparatus is still further configured to allow the controller to control an optical axis along which the visible light beam travels toward the eyeball, so as to follow an actual pupil position, based on the tracked pupil position.

This apparatus, therefore, would make it easier to ensure that the visible light travels through the pupil up to the retina without unintended interruption, even when the visible light is deviated from the pupil with a greater ease, due to the difficulty in enlarging the diameter of the visible light emerging from the scanner, in exchange for an increase in a scan rate by reducing the inertia of a movable part of the scanner.

In this apparatus, visible light is thrown at the eyeball for the purpose of displaying a desired image, while non-visible light is thrown at the eyeball for the purpose of detecting or tracking a pupil position.

This apparatus, therefore, would allow the pupil position to be tracked unnoticeably.

Further, this apparatus is configured to include a combination of the scanner and the guide, commonly for both the visible light and the non-visible light. In other word, an optical path extending from the scanner through the guide up to the eyeball is shared with both the visible and non-visible light, resulting in the achievement of downsizing, structural simplification, and cost reduction of this apparatus with greater ease than when those two different kinds of light require respective exclusive optical paths.

This apparatus according to the present mode may be practiced such that the non-visible light is directed to the eyeball at a time coincident with or different from that of the visible light.

The apparatus according to the present mode may be practiced in combination with the device according to any one of the above modes (2) to (7).

(9) The apparatus according to mode (8), wherein the intensity of the reflected light beam represented by the intensity signal outputted from the detector has first intensity changes dependent on position changes of the light beam along the individual scan lines, and second intensity changes dependent on position changes of the light beam across the scan lines, and the controller tracks a two-dimensional pupil position based on the first and second intensity changes of the reflected light beam, and controls or steers the optical axis along which the visible light beam travels toward the eyeball, so as to follow the actual pupil position, based on the tracked pupil position.

Similarly with the device constructed according to the previous mode (2), this apparatus constructed according to the present mode is configured such that the intensity of a portion of the light beam entering the surface of the eyeball which is reflected from the eyeball is detected as an intensity of reflected light beam, and such that a two-dimensional position of the pupil is determined or tracked based on first intensity changes in the detected intensity of reflected light beam, which are dependent on position changes of the light beam along the individual scan lines, and second intensity changes in the detected intensity of reflected light beam, which are dependent on position changes of the light beam across the scan lines.

(10) The apparatus according to mode (8) or (9), wherein the scanner scans the non-visible light beam entering the scanner, to thereby emit scanning non-visible light, the apparatus further comprising a focus adjuster adjusting a focus position of the emitted scanning non-visible light so as to be located on an optical axis extending between the scanner and the retina, at a predetermined distance from the pupil.

The apparatus would provide the same function and results as the device constructed according to the previous mode (4).

(11) The apparatus according to mode (10), wherein the focus adjuster is disposed at the guide.

This apparatus, because of the focus adjuster being located optically downstream from the scanner, would allow the likelihood that the focus adjuster could adversely affect the visible light, to be eliminated with greater ease than when the focus adjuster is located exactly at the scanner or optically upstream from the scanner.

(12) The apparatus according to mode (11), wherein the focus adjuster is disposed at an optically downstream part of the guide.

This apparatus, because of the focus adjuster being located at an optically downstream part of the guide, would allow the likelihood that the focus adjuster could adversely affect the visible light, to be eliminated with greater ease than when the focus adjuster is located at an optically upstream part of the guide or optically upstream from the guide.

(13) The apparatus according to mode (11) or (12), wherein the focus adjuster is configured to include at least one of a lens made of a glass material having a wavelength-dependent dispersion characteristic, and a diffractive element.

This apparatus would allow the visible light beam and the non-visible light beam, despite that these beams both enter common optics, to emit from the optics in differed directions. As a result, this apparatus would also allow the scanning visible light produced by the visible light beam and the scanning non-visible light produced by the non-visible light beam, to be focused at differed positions within the eyeball.

(14) The apparatus according to any one of modes (8)-(13), wherein the guide is configured to include a relay optical system.

(15) The apparatus according to any one of modes (8)-(14), wherein the controller includes optics disposed optically downstream of and away from the scanner.

This apparatus would allow a portion of the optical axis of the visible light beam located between the optics of the controller and the scanner, to be controlled by the optics, with the result that the control can be prevented from affecting a portion of the optical axis of the visible light beam located between the scanner and an optically upstream side from the scanner, with greater ease.

(16) The apparatus according to mode (15), wherein the scanner scans the visible light beam entering the scanner, to thereby emit scanning visible light, and the optics includes a deflector which is disposed at a focus position of the emitted scanning visible light and which deflects the optical axis along which the scanning visible light travels.

(17) The apparatus according to mode (16), wherein the deflector is configured to include at least one of a variable prism, an oscillating mirror, and a variable diffraction grating.

(18) The apparatus according to mode (15), wherein the scanner scans the visible light beam entering the scanner, to thereby emit scanning visible light, and the optics includes a parallel shifter effecting a parallel shifting of the optical axis along which the emitted scanning visible light travels, in a perpendicular direction to the optical axis.

(19) The apparatus according to mode (18), wherein the parallel shifter is configured to include a movable mirror which is inclined with respect to the optical axis and which is to be translated in the perpendicular direction.

(20) The apparatus according to any one of modes (8)-(19), wherein the controller tracks the pupil position and controls the optical axis in one direction, and the composite light beam is configured to have a cross section with a generally flattened shape extending perpendicular to the one direction.

This apparatus may be implemented in an arrangement in which the flattened cross section of the composite light beam has different extents measured in different directions, and in which a largest one of those extents is defined to be equal in size to or larger than the diameter of the pupil. In this regard, the dimension of the largest extent may be the length of a major or longer one of axes of an elongated circle or an ellipse, for example.

In this arrangement, for a desired image to be formed, the scanner is required to at least scan the composite light beam one-dimensionally in a direction perpendicular to an elongation direction of the largest extent.

In this arrangement, therefore, the tracking of the pupil position and follow-up control of an optical axis of the visible light beam are required to be performed at least with respect to a one-dimensional scan direction of the composite light beam. In this regard, the follow-up control is performed for controlling the optical axis along which the visible light beam travels to follow the actual pupil position.

As a result, this arrangement would achieve system simplification and high-speed processing of the pupil-position tracking and the follow-up control with greater ease than when the pupil-position tracking and the follow-up control are required to be performed two-dimensionally.

(21) The device according to any one of modes (1)-(7), wherein the light beam is scanned over the eyeball across its iris, the intensity changes of the reflected light beam are each caused by a scan of the light beam across the iris, and the intensity signal has level changes caused by the intensity changes of the reflected light beam.

(22) The device according to any one of modes (1)-(7) or mode (21), wherein the intensity signal is detected in association with a corresponding one of the scan lines, and the processor determines the two-dimensional position of the pupil based on a position of a high-level portion of the intensity signal and a position of the corresponding scan line.

Several presently preferred embodiments of the invention will be described in more detail by reference to the drawings in which like numerals are used to indicate like elements throughout.

Referring first to FIG. 1, there is schematically illustrated a retinal scanning display (hereinafter, abbreviated to "RSD") constructed according to a first embodiment of the present invention.

This RSD is a type of an image display apparatus of which allows a laser beam to be projected onto a retina 14 through a pupil 12 of a viewer's eye (i.e., an eyeball 10), to thereby let the viewer to perceive a display object via a virtual image.

More specifically, this RSD allows a laser beam to pass through the pupil 12 and to be focused on the retina 14, with its wavefront curvature and light intensity being properly modulated, and to be two-dimensionally scanned on the retina 14, to thereby project an image directly onto the retina 14.

As illustrated in FIG. 1, this RSD includes a light source unit 20, and a wavefront-curvature modulating optical system 22 and a scanning unit 24 both of which are disposed between the light source unit 20 and the viewer's eye 10, as arrayed in the description order.

This RSD further includes a pupil detector 30 for detecting or tracking the position (e.g., a center position) of the pupil 12, and a follow-up controller 32 for controlling an illumination light beam to follow the detected position of the pupil 12.

The follow-up controller 32 is a device for effecting adaptive control of a direction (or alternatively, an entrance position on the surface of the eye 10) of scanning light of the scanning unit 24 (i.e., ultimate output light of the RSD), to thereby achieve tracking-type imaging in which retinal scanning imaging is performed with an actual position of the pupil 12 being tracked.

The light source unit 20 will be firstly described below in more detail. For generating a laser beam of any color as a display-purpose laser beam (hereinafter, referred to also as "imaging light") by combining three laser beams of three primary colors (RGB) into a single laser beam, the light source unit 20 includes an R laser 40 emitting a red-colored laser beam, a G laser 42 emitting a green-colored laser beam, and a B laser 44 emitting a blue-colored laser beam.

The light source unit 20 further includes an infrared (IR) laser 46 emitting an infrared laser beam (hereinafter, referred to also as "infrared light") to be entered into the eye 10 for detecting the position of the pupil 12 with respect to the position of this RSD. These lasers 40, 42, 44, and 46 each may be constructed as a semiconductor laser, for example.

In the present embodiment, the red-colored laser beam, the green-colored laser beam, and the blue-colored laser beam each constitute an example of a visible light beam to be entered into the eye 10 for displaying an image. On the other hand, the infrared light constitutes an example of a non-visible light beam to be entered into the eye 10 for detecting the position of the pupil 12.

For laser beams emitted from the respective lasers 40, 42, 44, and 46 to be eventually combined, these laser beams are collimated by collimating optical systems 50, 52, 54, and 56, respectively, and thereafter, these laser beams are caused to enter respective dichroic mirrors 60, 62, 64, and 66, all of which are wavelength-selective. As a result, these laser beams are selectively reflected from or transmitted through the corresponding respective dichroic mirrors 60, 62, 64, and 66, depending on the wavelength of each laser beam.

More specifically, a red-colored laser beam (i.e., a first component of imaging light) emitted from the R laser 40 is caused to enter the dichroic mirror 60 after collimated by the collimating optical system 50. A green-colored laser beam (i.e., a second component of imaging light) emitted from the G laser 42 is caused to enter the dichroic mirror 62 through the collimating optical system 52. A blue-colored laser beam (i.e., a third component of imaging light) emitted from the B laser 44 is caused to enter the dichroic mirror 64 through the collimating optical system 54. The infrared light emitted form the IR laser 46 is caused to enter the dichroic mirror 66 through the collimating optical system 56.

Upon entry into the respective four dichroic mirrors 60, 62, 64, and 66, the imaging light (i.e., the laser beams of three primary colors) and the infrared light eventually enter the dichroic mirror 60, which is a representative one of the four dichroic mirrors 60, 62, 64, and 66, resulting in the laser beams being combined thereat. The combined laser beam is subsequently focused at a combining optical system 70.

While the optical section of the light source unit 20 has been described above, there will be described the electrical section of the light source unit 20.

The light source unit 20 includes a signal processing circuit 80. The signal processing circuit 80 is configured to perform signal processing in response to an externally-supplied video signal. The signal processing includes: signal processing for driving each of the lasers 40, 42, and 44; signal processing for modulating the curvature of wavefront of a laser beam, as described below; and signal processing for implementing a laser beam scan, as described below.

The signal processing circuit 80 generates (or extracts) signal components corresponding to the respective lasers 40, 42, and 44 (for red-colored light, green-colored light, and blue-colored light, respectively), based on an externally-supplied video signal. Further, the signal processing circuit 80 delivers desirable drive signals to the respective lasers 40, 42, and 44 via respective laser drivers 90, 92, and 94, based on the signal components for respective colors. As a result, an image is projected and displayed on the retina 14 with desired color and intensity in accordance with the externally supplied video signal.

Further, the signal processing circuit 80 generates (or extracts) a sync signal based on the aforementioned video signal, and delivers the sync signal to the scanning unit 24. The sync signal is used as a reference signal for scanning a laser beam and the infrared light.

Still further, the signal processing circuit 80 also delivers a depth signal based on depth information included in the aforementioned video signal, to the wavefront-curvature modulating optical system 22. The depth signal is used for controlling a wavefront-curvature modulator 110 described below.

The IR laser 46 is operated to emit the infrared light at a constant intensity. For causing the IR laser 46 to emit the infrared light, the signal processing circuit 80 supplies to the IR laser 46 via an IR laser driver 96, a drive signal which is used for causing the IR laser 46 to emit the infrared light at a constant intensity.

As a result, the amount of the infrared light entering the eye 10 is held constant, irrespective of the content of an image to be displayed. This prevents the accuracy of a pupil position being tracked from dropping due to fluctuations in the amount of light entering the eye 10.

In the present embodiment, the IR laser 46 is operated to emit the infrared light while an image is being displayed, during a period excluding a retrace and blanking period (i.e., a period excluding a horizontal retrace and blanking period, and excluding a vertical retrace and blanking period). The reasons why an emission period of the infrared light has been set in that manner will be described below in more detail The light source unit 20 which has been described above emits the imaging light and the infrared light from the combining optical system 70 at the same position. Upon combined and focused at the combining optical system 70, the imaging light and the infrared light pass sequentially through an optical fiber 100 functioning as a light transmitting medium, and a collimating optical system 104 which collimates a laser beam emerging divergently from the optical fiber 100 at its rearward end, and thereafter enters the wavefront-curvature modulating optical system 22.

The wavefront-curvature modulating optical system 22, which is an optical system for modulating the curvature of wavefront of a laser beam emitted from the light source unit 20, includes the wavefront-curvature modulator 110. Describing conceptually, the wavefront-curvature modulator 110 is constructed to principally include a combination of a converging lens and a mirror which is displaceable along the optical axis of the converging lens.

More specifically, as illustrated in FIG. 1, the wavefront-curvature modulator 110 includes a beam splitter 112 which the imaging light and the infrared light coming from the collimating optical system 104 enter, and a converging lens 114 which converges the imaging light coming from the beam splitter 112. The wavefront-curvature modulator 110 further includes a movable mirror 116 to modulate the curvature of wavefront of the imaging light coming from the converging lens 114.

This wavefront-curvature modulator 110 further includes an actuator 118 for displacing the movable mirror 116 along the optical axis. An example of the actuator 118 may be of a type employing a piezoelectric device. The actuator 118 moves the location of the movable mirror 116 in response to a depth signal (i.e., a Z signal) supplied from the signal processing circuit 80, to thereby modulate the curvature of wavefront of the imaging light coming from the wavefront-curvature modulator 110. Upon reflected from the movable mirror 116, the imaging light passes through the converging lens 114 and the beam splitter 112 to be directed to the scanning unit 24.

There is disposed between the beam splitter 112 and the converging lens 114 a dichroic mirror 120 which reflects the infrared light in a selective fashion. As a result, the infrared light incoming from the beam splitter 112 is reflected from the dichroic mirror 120 into a light entrance side, and passes through the beam splitter 112 again to be directed to the scanning unit 24.

For this reason, the curvature of wavefront of the infrared light is not modulated during an image display operation, with the result that the infrared light enters the surface of the eye 10 to form a light entrance region having a constant area. This prevents the accuracy of a pupil position being tracked to drop due to fluctuations in the area of the light entrance region.

As illustrated in FIG. 1, the imaging light and the infrared light, both emerging from the wavefront-curvature modulating optical system 22 constructed as described above, enter the aforementioned scanning unit 24. This scanning unit 24 includes a horizontal scanning system 130 and a vertical scanning system 132.

The horizontal scanning system 130 is an optical system which performs a raster scan allowing a laser beam to be scanned horizontally along a plurality of horizontal scan lines, per each frame of an image to be displayed. On the other hand, the vertical scanning system 132 is an optical system which performs a vertical scan allowing a laser beam to be scanned vertically from the first one toward the last one of the scan lines, per each frame of an image to be displayed.

More specifically, in the present embodiment, the horizontal scanning system 130 includes a polygon mirror 134 as a unidirectionally-rotating mirror causing mechanical deflection. The polygon mirror 134 is rotated about an axis of rotation which intersects with respect to the optical axis of a laser beam entered into the polygon mirror 134, at a higher rate, by means of a motor (not shown). The rotation of the polygon mirror 134 is controlled in response to a horizontal sync signal supplied from the signal processing circuit 80.

The polygon mirror 134r which includes a plurality of mirror facets 136 positioned about the axis of rotation of the polygon mirror 134, performs one cycle of deflection of a laser beam, each time the laser beam passes through one of the mirror facets 136. Upon deflection, the laser beam is relayed to the vertical scanning system 132 by a relay optical system 140. In the present embodiment, the relay optical system 140 includes a plurality of optical elements 142 and 144 in series along the optical path.

While the horizontal scanning system 130 has been described above, the vertical scanning system 132 includes a galvanometer mirror 150 as an angularly-oscillating mirror causing mechanical deflection. The galvanometer mirror 150 is arranged to allow a laser beam emerging from the horizontal scanning system 130, to be converged by the relay optical system 140 and enter the galvanometer mirror 150. The galvanometer mirror 150 is oscillated about an axis of rotation intersecting with respect to the optical axis of the laser beam entering the galvanometer mirror 150. The start-up timing and the rotational speed of the galvanometer mirror 150 are controlled in response to a vertical sync signal supplied from the signal processing circuit 80.

The horizontal scanning system 130 and the vertical scanning system 132 both described above cooperate to effect a two-dimensional scan of composite light comprised of the imaging light and the infrared light, whereby the scanned composite light impinges on the viewer's eye 10 via a relay optical system 160. The relay optical system 160 includes optical elements 162 and 164 on an upstream and a downstream side on the optical path of the relay optical system 160, respectively Typically, each of the optical elements 162 and 164 is in the form of a lens.

As illustrated in FIG. 1, after combined and focused at the combining optical system 70, the imaging light and the infrared light pass through the wavefront-curvature modulating optical system 22, the scanning unit 24, and the relay optical system 160, in this description order, and eventually enter the viewer's eye 10. In this stage, the imaging light and the infrared light travel along the same optical path between the combining optical system 70 and the eye 10.

That is to say, the infrared light, which is thrown at within the eye 10 for detecting a pupil position, travels between the light source unit 20 and the eye 10 along an optical path shared with the imaging light. This allows this RSD to be built up with added and modified components to a standard configuration of an RSD being as few as possible.

Figure 2:
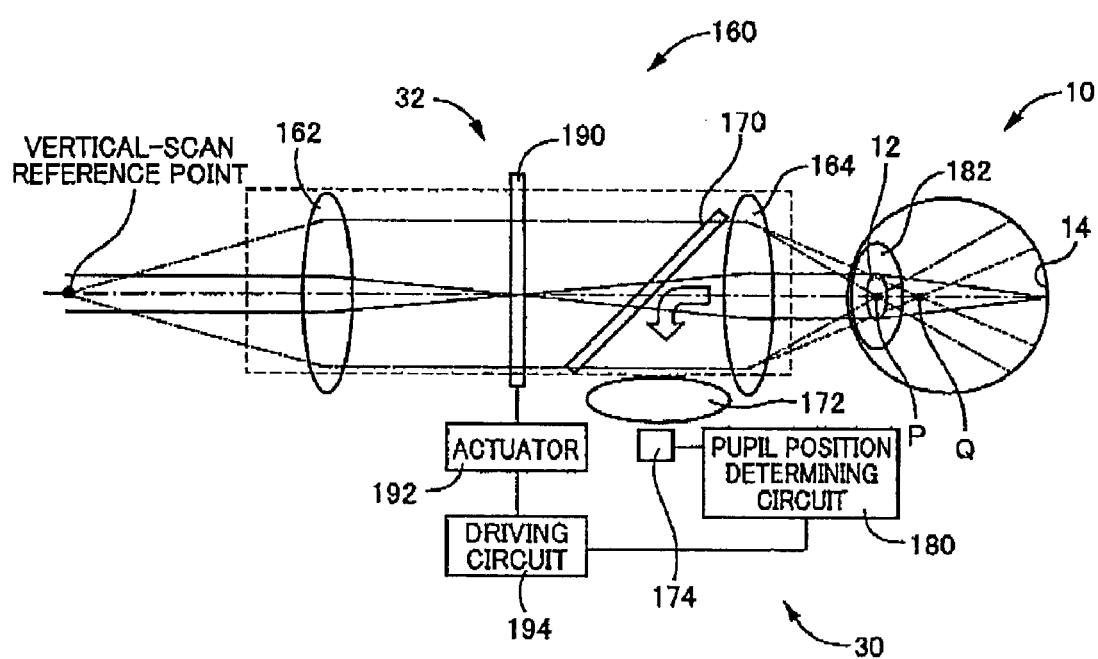
FIG. 2 is an optical path diagram illustrating a path along which light is directed from a galvanometer mirror 150, by way of a relay optical system 160, toward an eye 10 of a viewer, with a pupil 12 of the viewer facing forward, the path being located within the retinal scanning display depicted in FIG. 1.

As described above, this RSD includes the pupil detector 30. As illustrated in FIG. 2, this pupil detector 30 includes: an infrared semi-transparent mirror 170 disposed between the two optical elements 162 and 164; a lens 172 which converges reflected light from the infrared semi-transparent mirror 170; and a photodiode 174 (an example of a photo sensor) for receiving outgoing light from the lens 172 and outputting a signal indicative of the intensity of the outgoing light, as a return-light detection signal.

Incident light on the photodiode 174 is a portion of the infrared light entering the eye 10 which is reflected from the surface of the eye 10 and then returns to the light entrance side, which portion is return light (an example of the aforementioned "reflected light beam"). The return-light detection signal, which is outputted from the photodiode 174 based on the intensity of the return light, is a time series signal indicative of a time-varying intensity of the return light.

As described above, the IR laser 46 emits the infrared light while an image is being displayed, during a period excluding a retrace and blanking period (i.e., a period excluding a horizontal retrace and blanking period, and excluding a vertical retrace and blanking period). Therefore, in the present embodiment, the infrared light is scanned on the surface of the eye 10 only along a plurality of effective horizontal scan lines (i.e., a plurality of horizontal scan lines which would be perceived by the viewer if the infrared light were visible light).

As a result, the return-light detection signals outputted from the photodiode 174 are obtained in association with the plurality of effective horizontal scan lines, respectively, on a common time scale. The effective horizontal scan lines and blanked horizontal retrace lines, in comparison, are different in scan rate.

For this reason, if a pupil position is tracked based on a return-light detection signal, without any care about the existence of the scan rate difference, irrespective of whether it is during an effective scan period or a blanking period, then tracking errors occur due to the time scale difference.

The infrared semi-transparent mirror 170 described above allows the imaging light and the infrared light concurrently coming from an optical upstream side of the semi-transparent mirror 170, to pass through the infrared semi-transparent mirror 170 toward an optical downstream side of the infrared semi-transparent mirror 170.

In addition, the infrared semi-transparent mirror 170 reflects into the lens 172, the infrared light which is reflected from the surface of the eye 10 and which then enters the infrared semi-transparent mirror 170 from the optical downstream side of the infrared semi-transparent mirror 170, in the form of scattered infrared light.

The pupil detector 30 further includes a pupil position determining circuit 180 which determines the position of the pupil 12 using the intensity of the infrared light reflected from the viewer's eye 10, based on a return-light detection signal outputted from the photodiode 174. The function of the pupil position determining circuit 180 will be described below in more detail.

In the relay optical system 160, the optical element 162 is a first-stage lens, while the optical element 164 is a last-stage lens. The last-stage lens 164 is an optical element which has a wavelength-dependent dispersion characteristic (i.e., a characteristic that the refractive index and therefore the refracting power depend on the wavelength of the incoming light). Such an optical element is referred to in the art as a wavelength dispersive element.

The optical element is made of a glass material having a characteristic that the refractive index and therefore the refracting power selectively decreases in a range of a long wavelength, which is to say, the wavelength of the infrared light.

The last-stage lens 164 is configured such that the imaging light is caused to be converged at the position of the pupil 12 (crystal lens), while the infrared light is caused to be converged at a position a little farther from the position of the pupil 12 (crystal lens) to a near side to the retina 14.

This allows the infrared light to be scanned on the surface of the eye 10 in a region larger than that in which the imaging light is scanned. This will be described below in more detail.

As illustrated in FIG. 2, a light beam is angularly oscillated over a maximum scan angle by means of the vertical scanning system 132.

When a scanning light beam produced by the vertical scanning system 132 (i.e., an instantaneous beam emerging from the vertical scanning system 132) travels along the optical axis, the scanning light beam travels along a straight line so as to pass through the first-stage lens 162, the last-stage lens 164, and the pupil 12, and then enters the retina 14 In this case, the scanning light beam, because of the possession of its cross sectional area, is converged and focused by the first-stage lens 162, and is then transformed into the original parallel light beam by the second stage lens 164. The parallel light beam travels through the pupil 12 and is focused at the retina 14.

When a scanning light beam produced by the vertical scanning system 132 (i.e., an instantaneous beam emerging from the vertical scanning system 132) is instantaneously positioned at the maximum scan angle, the scanning light beam travels along a common optical path which is bent at each of the lenses 162 and 164, irrespective of whether the scanning light is the imaging light or the infrared light, and then enters the eye 10.

When a scanning light beam (i.e., an instantaneous beam) emerging from the vertical scanning system 132 is, however, a light beam of imaging light, the center line of the scanning light beam ideally passes through the center of the pupil 12 (i.e., the center of the crystal lens) and then enters the retina 14.

That is to say, scanning imaging light (i.e., scanning visible light) emerging from the vertical scanning system 132 (i.e., a trace of a spot of a deflected beam angularly oscillated during vertical scan) is ideally converged at a position "P" in the pupil 12.

On the other hand, when a scanning light beam emerging from the vertical scanning system 132 is the infrared light, scanning infrared-light (i.e., scanning non-visible light) emerging from the vertical scanning system 132 (i.e., a trace of a spot of a deflected beam angularly oscillated during vertical scan) is converged at a position Q farther from the pupil 12 to the retina 14. As a result, the scanning infrared-light enters the surface of the eye 10 in a region large enough to include the pupil 12 and an iris 182.

Accordingly, in the present embodiment, despite that the imaging light and the infrared light travel along the same optical path between the light source unit 20 and the viewer's eye 10, the fact that the last-stage lens 164 is wavelength-selective allows the infrared light to be scanned on a two-dimensional scan region located on the surface of the eye 10 with an area large enough to include the pupil 12 and the iris 182, without adversely affecting a focal position of the imaging light within the eye 10.

As described above, the RSD further includes the follow-up controller 32. The follow-up controller 32 includes: a variable prism 190 which is an example of an optical-axis shifter; an actuator 192 for changing the shape of the variable prism 190; and a driving circuit 194 for driving the actuator 192. The driving circuit 194 is coupled to the pupil position determining circuit 180 of the aforementioned pupil detector 30.

The follow-up controller 32, although will be described below in more detail, shifts the optical axis of the imaging light two-dimensionally in a primary scan direction and a secondary scan direction by the use of the variable prism 190, the actuator 192, and the driving circuit 194, and by referencing a signal supplied from the pupil position determining circuit 180, to thereby control or steer the optical axis to follow the actual position of the pupil 12.

As illustrated in FIG. 2, the variable prism 190 is disposed between the two lenses 162 and 164, at a focus position of light emerging from the first-stage lens 162. The placement of the variable prism 190 at the focal position resultantly allows light emerging from the first-stage lens 162 to remain unchanged in terms of the curvature of wavefront, even after passing through the variable prism 190.

Figure 3:
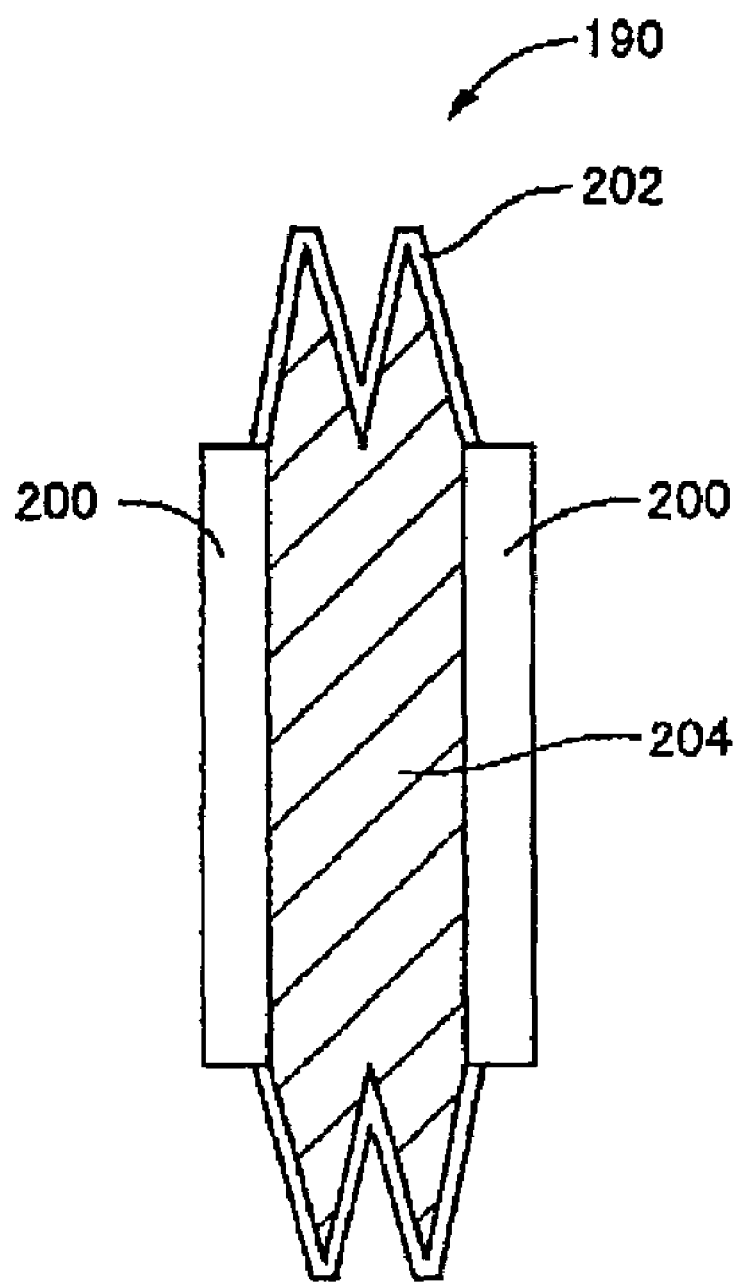
FIG. 3 is a side sectional view illustrating a variable prism 190 depicted in FIG. 2.

As illustrated in FIG. 3, the variable prism 190 includes two plate glasses 200 and 200, which are opposed to each other in a thickness-wise direction of the variable prism 190 with a space left between the glasses 200 and 200. The plate glasses 200 and 200 are joined together at their circumferences via a flexible bellows body 202 (e.g., film-shaped bellows made of a synthetic resin), with a sealed space between the plate glasses 200 and 200 being defined. The sealed space is filled with a high refractive index liquid 204.

The bellows body 202 is expanded and contracted (collapsed) by the actuator 192, causing the bellows body 202 to change its shape, and accordingly, causing the imaging light entering the variable prism 190 to change an angle at which the imaging light exits the variable prism 190, as well.

Figure 4:
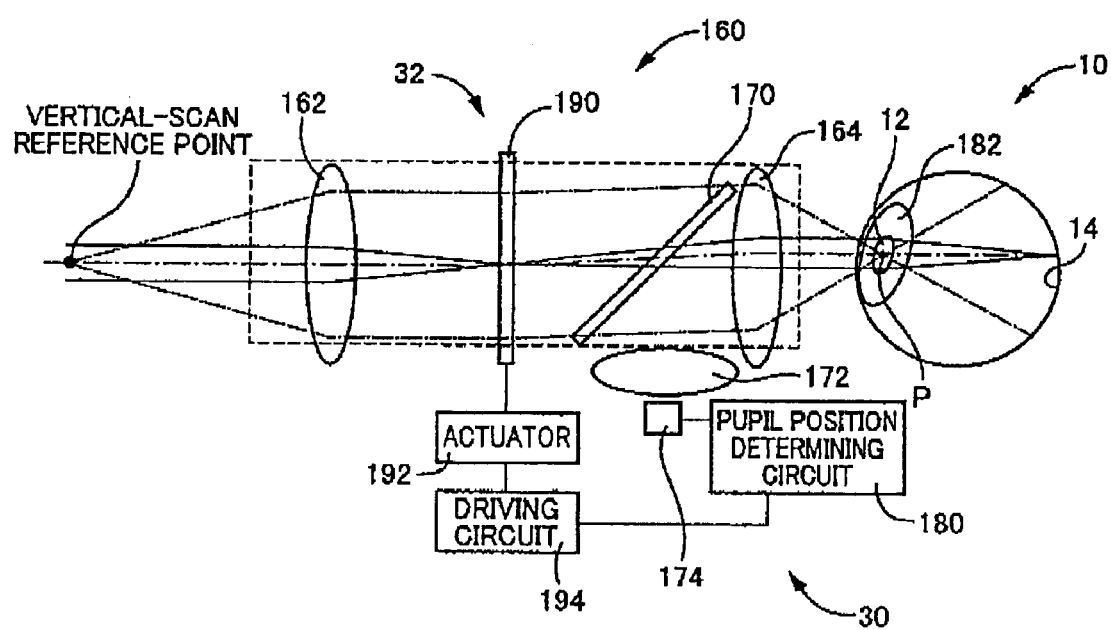
FIG. 4 is an optical path diagram illustrating a path along which light is directed from the galvanometer mirror 150, by way of the relay optical system 160, toward the eye 10 of the viewer, with the pupil 12 facing obliquely upward, the path being located within the retinal scanning display depicted in FIG. 1.

FIG. 4 illustrates an example in which the optical axis of the imaging light is shifted to follow the position of the pupil 12 when the pupil 12 is facing slightly obliquely upward rather than when facing forward. The optical-axis follow-up control allows the imaging light to pass through the pupil 12 and to be focused at the retina 14, wherever the actual position of the pupil 12 is.

Then, the function of the pupil position determining circuit 180 will be described in more detail below.

Firstly describing schematically, the pupil position determining circuit 180 detects or tracks the two-dimensional position of the pupil 12, based on first and second intensity changes of the aforementioned return light. The first intensity changes depend on position changes of the return light along the individual scan lines, while the second intensity changes depend on position changes of the return light across the scan lines.

The position of the pupil 12 is tracked based on the intensity of the return light, and the intensity of the return light changes as the position of the pupil 12 changes and the infrared light changes in intensity. The infrared light shares the optical axis with the imaging light, and therefore, any shifting of the optical axis of the imaging light results in a corresponding shifting of the optical axis of the infrared light. It therefore follows that the position of the pupil 12 is determined relative to the two-dimensional position of the optical axis located immediately before the optical axis is subsequently shifted.

As is well known, the pupil 12 is a circular opening in the center of the iris 182 which dilates and contracts in the shape of a circle. Once light enters the eye 10, the light is directed to the retina 14 through the pupil 12. The iris 182 dilates and contracts as a function of the amount of the light incident on the eye 10, with the resulting function of increasing and decreasing the pupil 12 in diameter. It is characteristic of the iris 182 to reflect incident light on the iris 182 with a high reflectance than that of the pupil 12.

When a viewer uses this RSD, the infrared light is scanned on the surface of the viewer's eye 10 along the individual scan lines. As described above, the scan region is defined to cover the pupil 12 with a size larger than that of the pupil 12, with the result that each scan line can pass through the pupil 12 and the iris 182 surrounding the pupil 12. As will be apparent from the above description, the infrared light is well reflected from the iris 182, while the infrared light is hardly reflected from the pupil 12.

When the infrared light is scanned along a scan line which passes through neither the pupil 12 nor the iris 182, the return light from the surface of the eye 10 is weak over the entire scan line. Therefore, in this case, the return-light detection signal outputted from the photodiode 174 has a relatively flat waveform, and the intensity (e.g., a voltage) of the return-light detection signal is at a low level over the entire scan line.

In contrast, when the infrared light is scanned along a scan line which passes through the iris 182 but not through the pupil 12, the return light from the surface of the eye 12 is strong in a portion of the scan line which passes through the iris 182, while the return light is weak in the remaining portion of the scan line.

For this reason, in this case, the return-light detection signal outputted from the photodiode 174 includes a high-level portion only in a sub-area corresponding to a portion of the scan line which passes through the iris 182. That is to say, in this case, the return-light detection signal corresponding to one scan line includes only one high-level portion, and has a signal waveform which exhibits a single peak.

Further, when the infrared light is scanned along a scan line which passes through both the pupil 12 and the iris 182, the return light from the surface of the eye 12 is strong in a portion of the scan line which passes through the iris 182, while the return light is weak in a portion of the scan line which passes through the pupil 12.

For this reason, in this case, the return-light detection signal outputted from the photodiode 172 includes high-level portions in sub-areas corresponding to two separate portions of the scan line. That is to say, in this case, the return-light detection signal corresponding to one scan line includes two high-level portions, and has a signal waveform which exhibits a double or twin peak.

For a scan line corresponding to a return-light detection signal having two high-level portions, a single low-level portion exists between the two high-level portions. The position of the low-level portion within the corresponding return-light detection signal indicates the position of the pupil 12 in a primary scan direction or a horizontal direction.

Further, a return-light detection signal corresponding to one of the scan lines which passes through one diameter portion of the pupil 12 or which is very close to the one diameter portion has a low-level portion larger in length than any other return-light detection signals.

In addition, if a scan-line number of any one of the scan lines is specified, then the position of the subject scan line is identified in a secondary scan direction or a vertical direction.

Therefore, a scan-line number of one of the scan lines corresponding to a return-light detection signal having a longest low-level portion indicates the position of the pupil 12 in a secondary scan direction or a vertical direction.

In light of the findings described above, a time series signal from the photodiode 174 enters the pupil position determining circuit 180 in association with a scan-line number n, and the pupil position determining circuit 180 tracks the two-dimensional position of the pupil 12 with respect to the position of this RSD.

It is added that, the pupil position determining circuit 180 may be configured to track a view direction when the pupil 12 is not facing forward, by comparing the position of the pupil 12 detected when the pupil 12 is facing forward direction, with the position of the pupil 12 detected when the pupil 12 is not facing forward.

The pupil position determining circuit 180 further includes, in addition to the aforementioned pupil-position tracking, the optical-axis follow-up control allowing the optical axis of the imaging light to be controlled to follow a pupil position.

Figure 12:
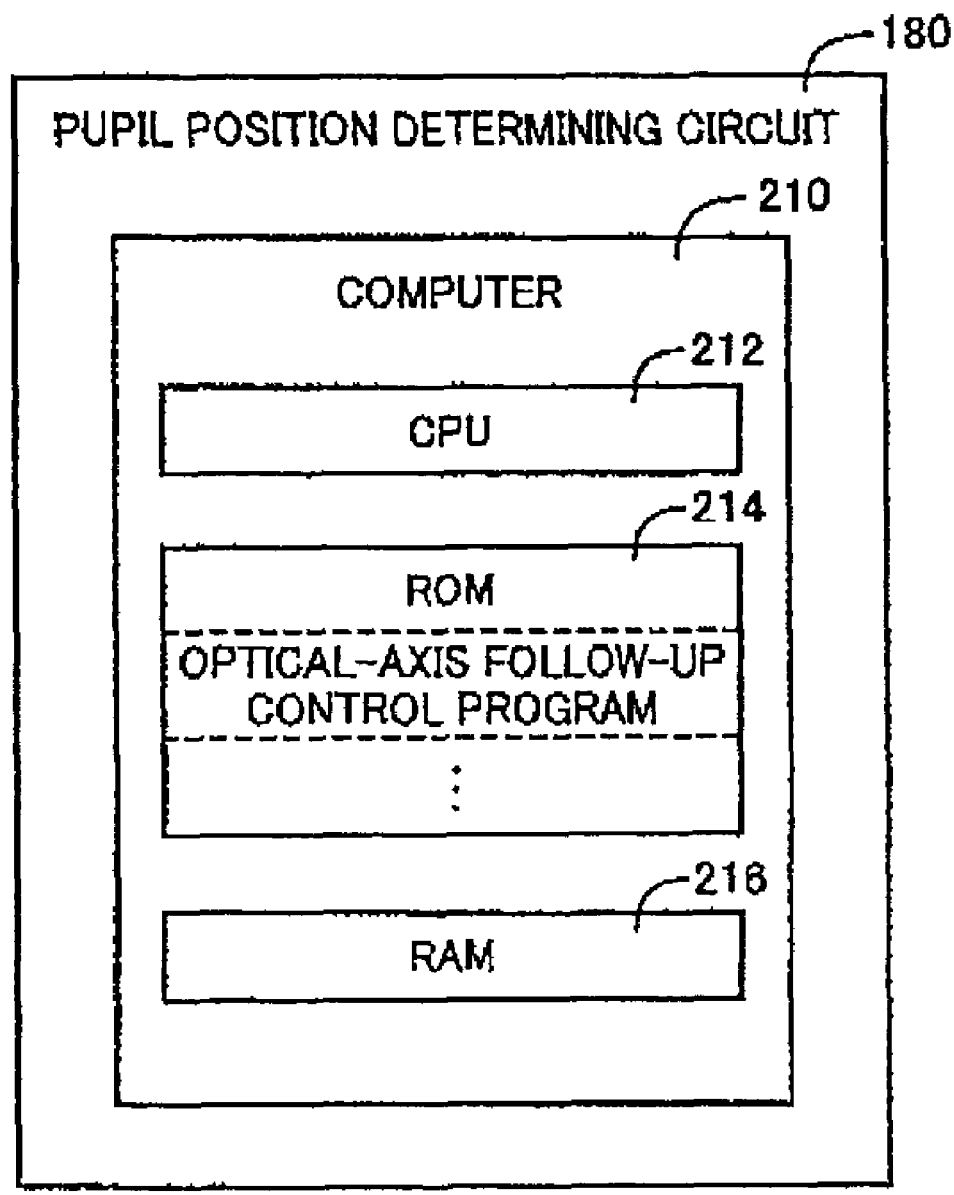
FIG. 12 is a schematic block diagram illustrating the hardware configuration of the pupil position determining circuit 180 depicted in FIGS. 1 and 2.

In order to accomplish these functions, the pupil position determining circuit 180, as illustrated in FIG. 12, includes a computer 210 incorporating a Central Processing Unit (CPU) 212, a Read Only Memory (ROM) 214, and a Random Access Memory (RAM) 216. The CPU 212 executes an optical-axis follow-up control program stored in the RAM 214.

Figure 5:
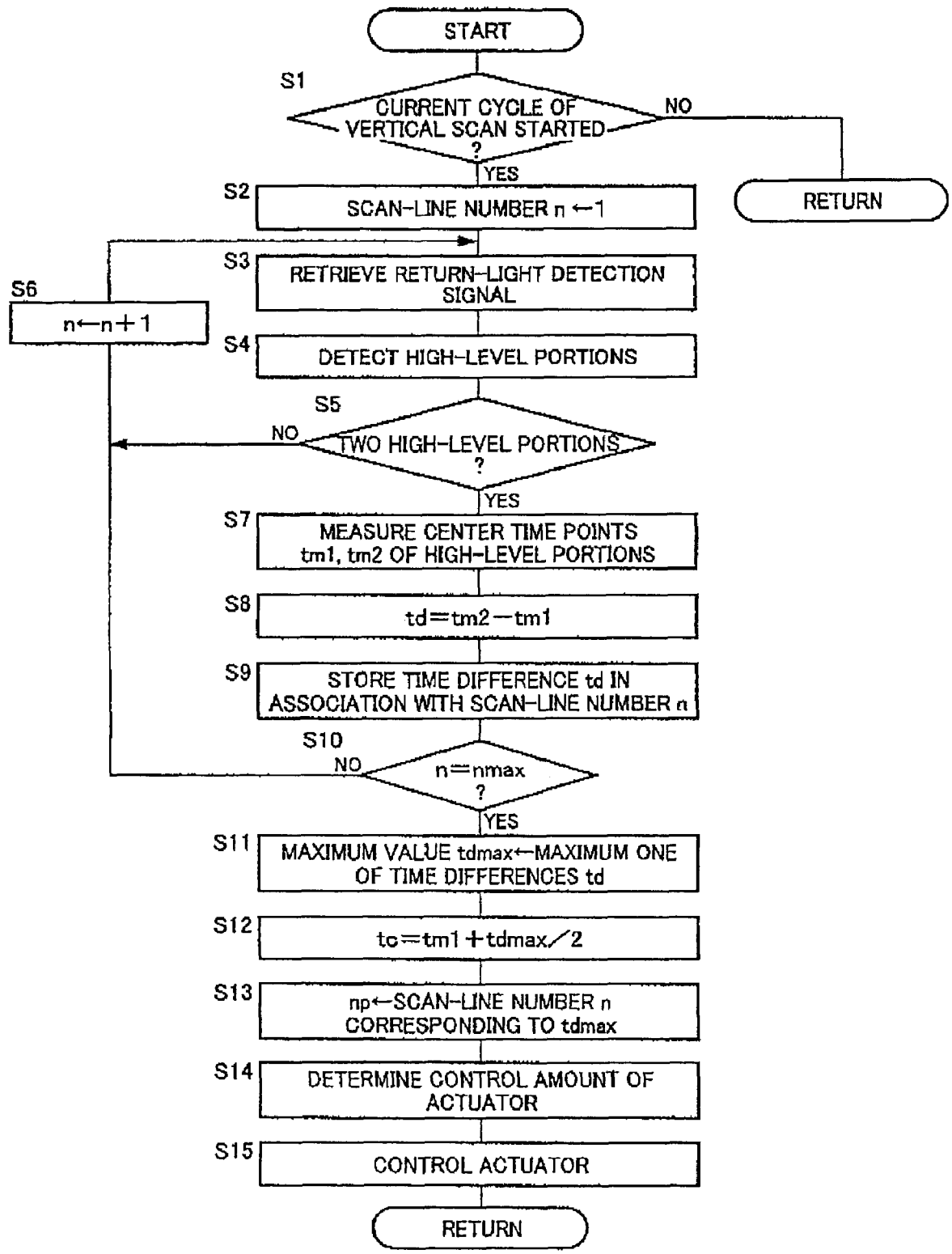
FIG. 5 is a flow chart conceptually illustrating an optical-axis follow-up control program executed by a computer in a pupil position determining circuit 180 depicted in FIG. 2.

In FIG. 5, there is conceptually illustrated in flow chart the optical-axis follow-up control program.

This optical-axis follow-up control program is repetitively executed by the computer 210. Each cycle of the optical-axis follow-up control program begins with a step S1 to determine whether or not a vertical scan has been initiated for a current image frame. That is to say, a determination is made as to whether or not a horizontal scan has been initiated for the first scan line belonging to the current image frame.

If a horizontal scan has not been initiated for the current image frame, then the determination of the step S1 becomes "NO," then one cycle of the optical-axis follow-up control program is terminated immediately. On the other hand, if a horizontal scan has been initiated for the current image frame, then the determination of the step S1 becomes "YES," with progress to a step S2.

At this step S2, a scan-line number n is set to "1." Thereafter, at a step S3, a return-light detection signal in the form of a time series signal is retrieved from the photodiode 174 in association with the current scan-line number n Subsequently, at a step S4, an attempt is made to detect a high-level portion of the return-light detection signal which has been retrieved in association with the current scan-line number n. The high-level portion is a portion of the return-light detection signal, the intensity of which exceeds a predetermined threshold value.

Thereafter, at a step S5, a determination is made as to whether or not the number of the detected high-level portions is equal to two.

Figure 6:
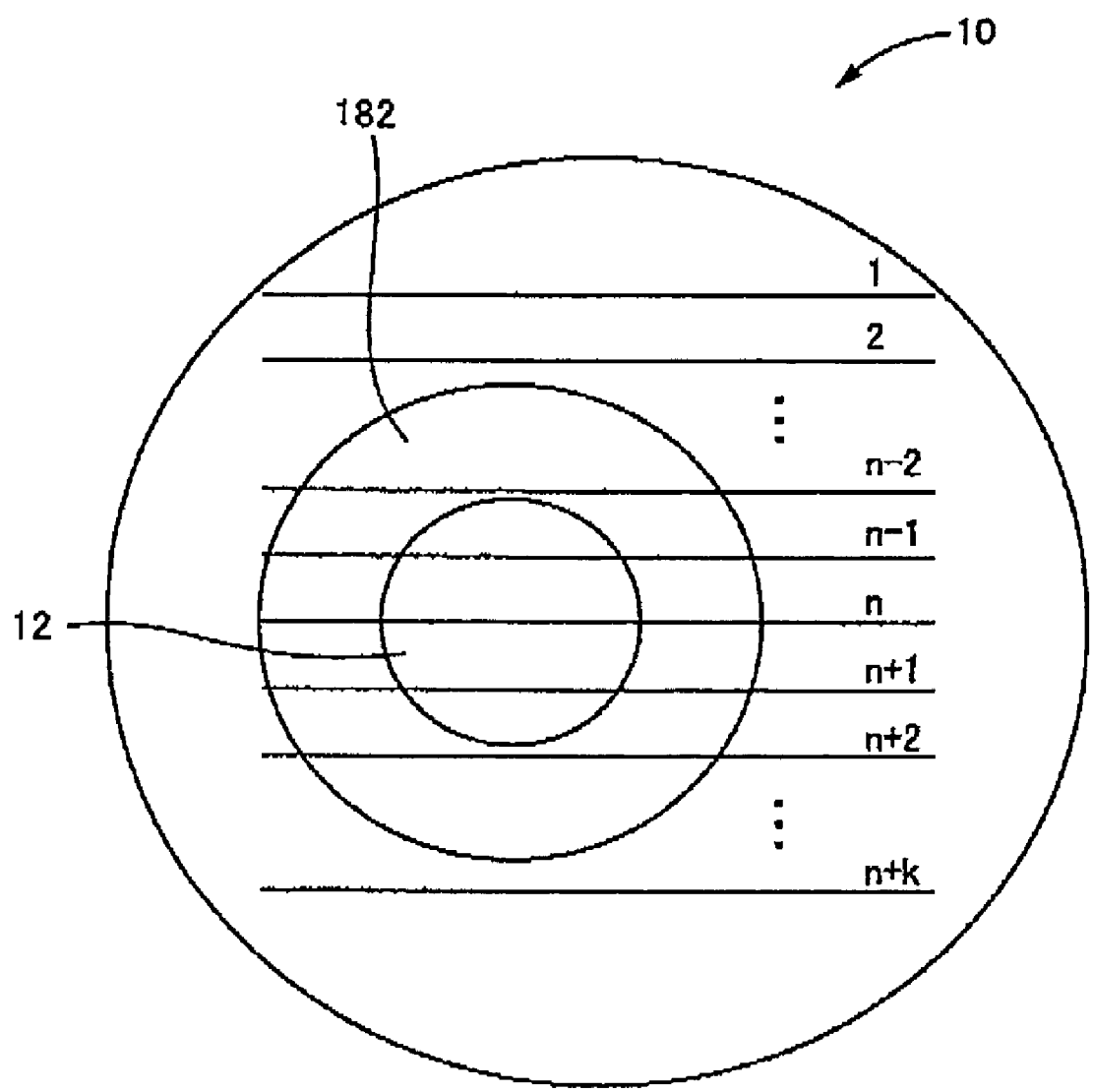
FIG. 6 is a front view, for explanation of a principle in which the position of the pupil 12 is tracked as a result of the execution of the optical-axis follow-up control program depicted in FIG. 5, illustrating a trace of a spot of infrared light scanned on the surface of the eye 10 of the viewer.
Figure 7:
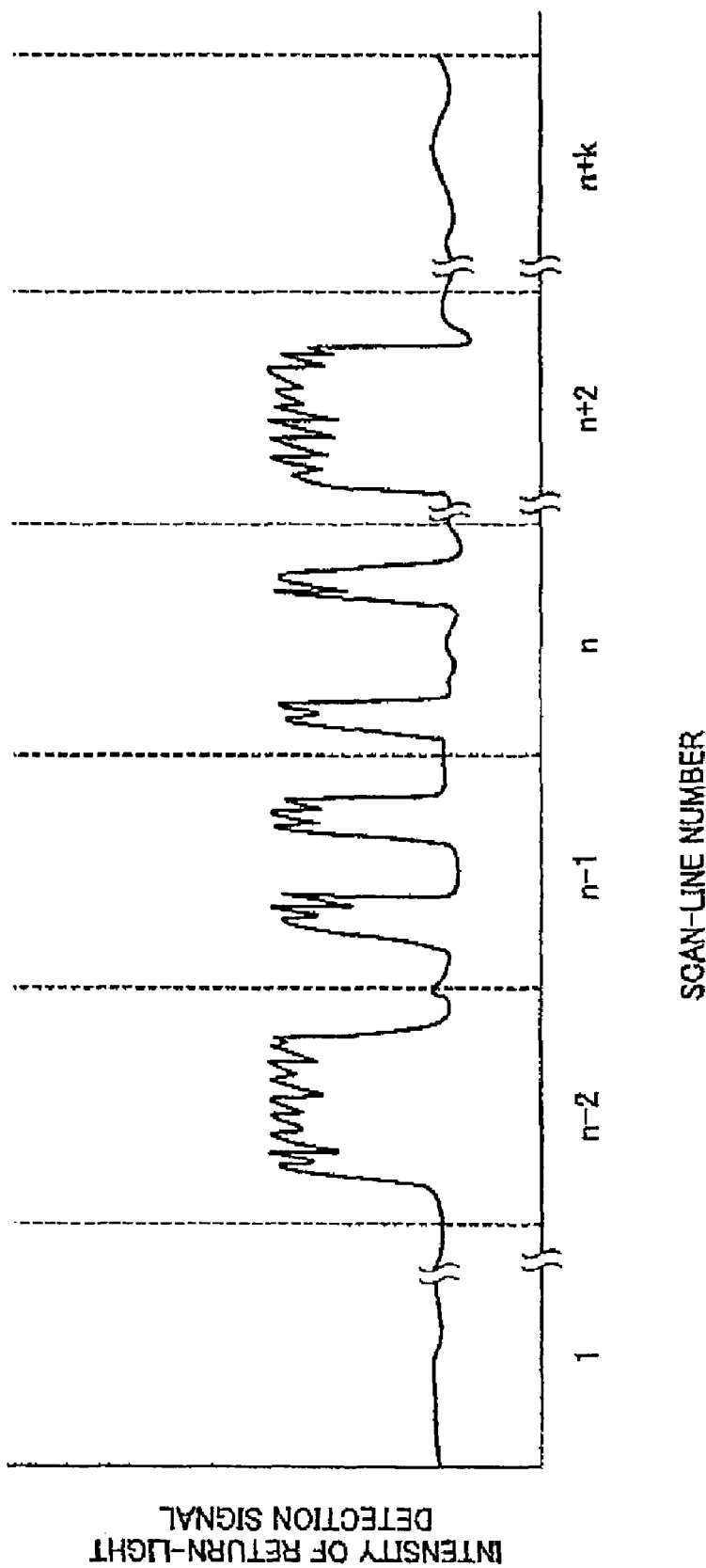
FIG. 7 is a graph illustrating a relationship between the intensities of a return-light detection signal captured as a result of the implementation of a step S3 depicted in FIG. 5, and scan-line numbers.

As illustrated in FIG. 6, the first scan line (a scan line whose scan-line number n is "1") passes through neither the pupil 12 nor the iris 182, and therefore, a return-light detection signal corresponding to the first scan line has no high-level portion, as illustrated in FIG. 7 in which the current scan line is denoted by "1" of the scan line number.

If the number of the detected high-level portions is zero or one, then the determination of the step S5 becomes "NO," resulting in the implementation of a step S6 to increment the scan-line number n by one. Thereafter, the program returns to the step S3 to retrieve from the photodiode 174 a return-light detection signal associated with the next scan line.

If, as a result of a horizontal scan having been repeated some times for the same image frame, one of the scan lines has passed through only the iris 182, not through the pupil 12, as illustrated in FIG. 6 in which the current scan line is denoted by "n−2" of A scan-line number, then a return-light detection signal corresponding to the current scan line occurs to have a single high-level portion, as illustrated in FIG. 7 in which the current scan line is denoted by "n−2" of a scan-line number.

If, as a result of a horizontal scan having been further repeated some times for the same image frame, one of the scan lines has passed through both the pupil 12 and the iris 182, as illustrated in FIG. 6 in which the current scan line is denoted by "n" of a scan-line number, then a return-light detection signal corresponding to the current scan line occurs to have two high-level portions, as illustrated in FIG. 7 in which the current scan line is denoted by "n" of a scan-line number.

If the number of the detected high-level portions is two, then the determination of the step S5 becomes "YES," and the program proceeds to a step S7. At the step S7, measurements are obtained of a center time point tm1 of the time width of a leading one of two high-level portions, and a center time point tm2 of the time width of a trailing one of the two high-level portions.

Following that, at a step S8, a time difference td between the detected two high-level portions is determined as the difference between the measured center time points tm1 and ta2. Thereafter, at a step S9, a value of the time difference td is stored in the RAM 216 in association with the current scan-line number n.

Thereafter, at a step S10, a determination is made as to whether or not the current scan line is the last scan line for the current image frame. That is to say, a determination is made as to whether or not the current scan-line number n is equal to a maximum value nmax. If the current scan-line number n is not equal to the maximum value nmax, then the determination of the step S10 becomes "NO," and the program proceeds to S6 to increment the scan-line number n by one in preparation for the next cycle of a horizontal scan. Subsequently, the program returns to the step S3.

The execution of steps S3-S10 is repeated until the current scan-line number n reaches the maximum value nmax. If the current scan-line number n reaches the maximum value nmax, then the determination of the step S10 becomes "YES."

Figure 8:
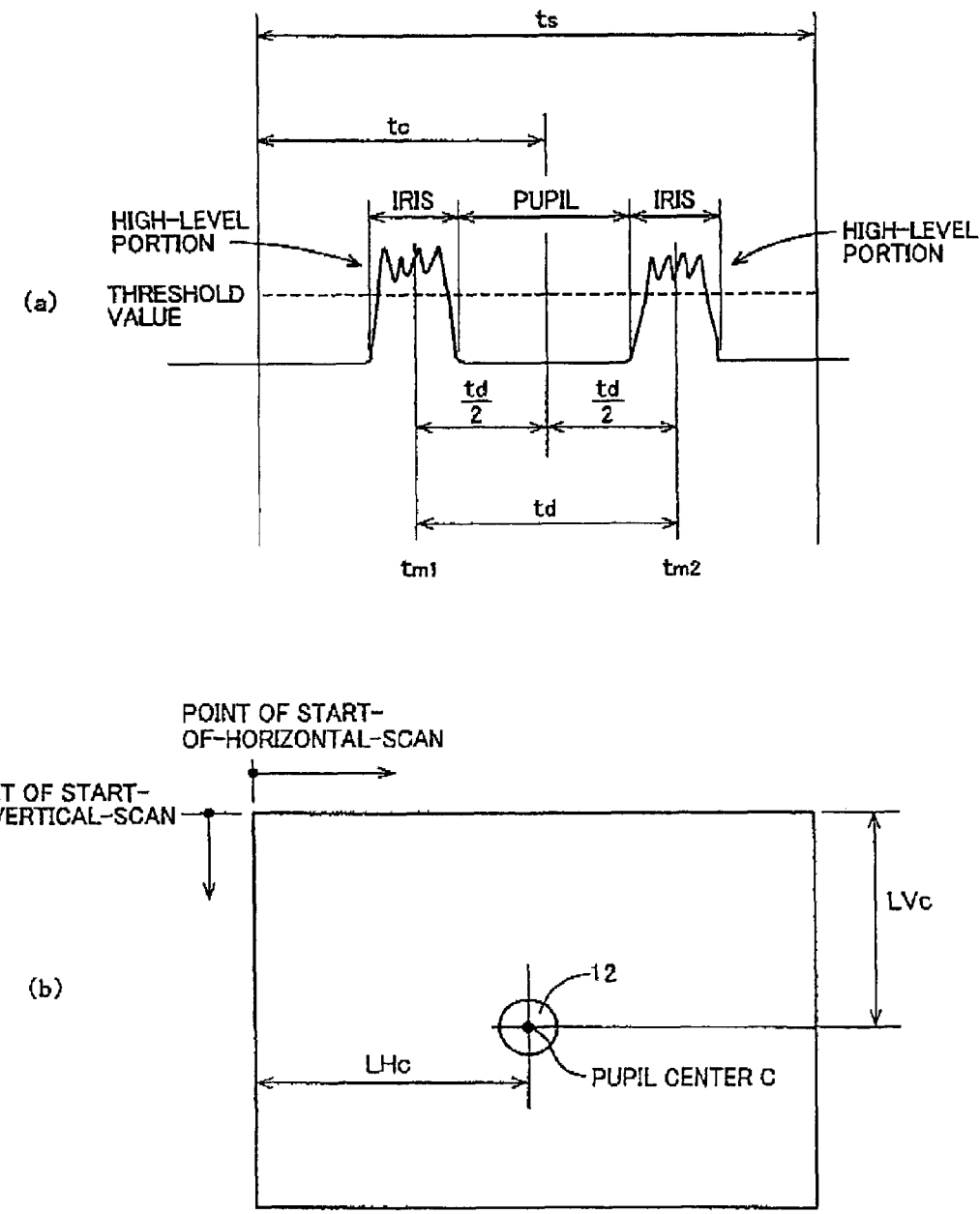
FIG. 8(a) is a graph indicating an exemplary waveform of the return-light detection signal depicted in FIG. 7.
FIG. 8(b) is a view for explaining the position of the pupil 12 in association with the waveform characteristics of the return-light detection signal.

Referring now to FIG. 8, a relationship will be described between positions LHc and LVc of the pupil 12 and time-related information tm1, tm2, td, and tc related to the high-level portions.

As illustrated in FIG. 8(a), a time tc elapsed from a start time of the subject return-light detection signal up to a middle time point between the two high-level portions is determined by adding one-half the time difference td between the detected two high-level portions, to the center time point tm1 of the leading one of the two high-level portions.

As illustrated in FIG. 8(b), this elapsed time tc indicates a distance LHc of a pupil center C from a point of start-of-horizontal-scan on a corresponding one of the scan lines to the subject return-light detection signal.

As illustrated in FIG. 8(b), a scan-line number np assigned to one of the scan lines which corresponds to the time difference td having the maximum value tdmax indicates a distance LVc of the pupil center C from a point of start-of-vertical-scan on the current image frame.

Figure 9:
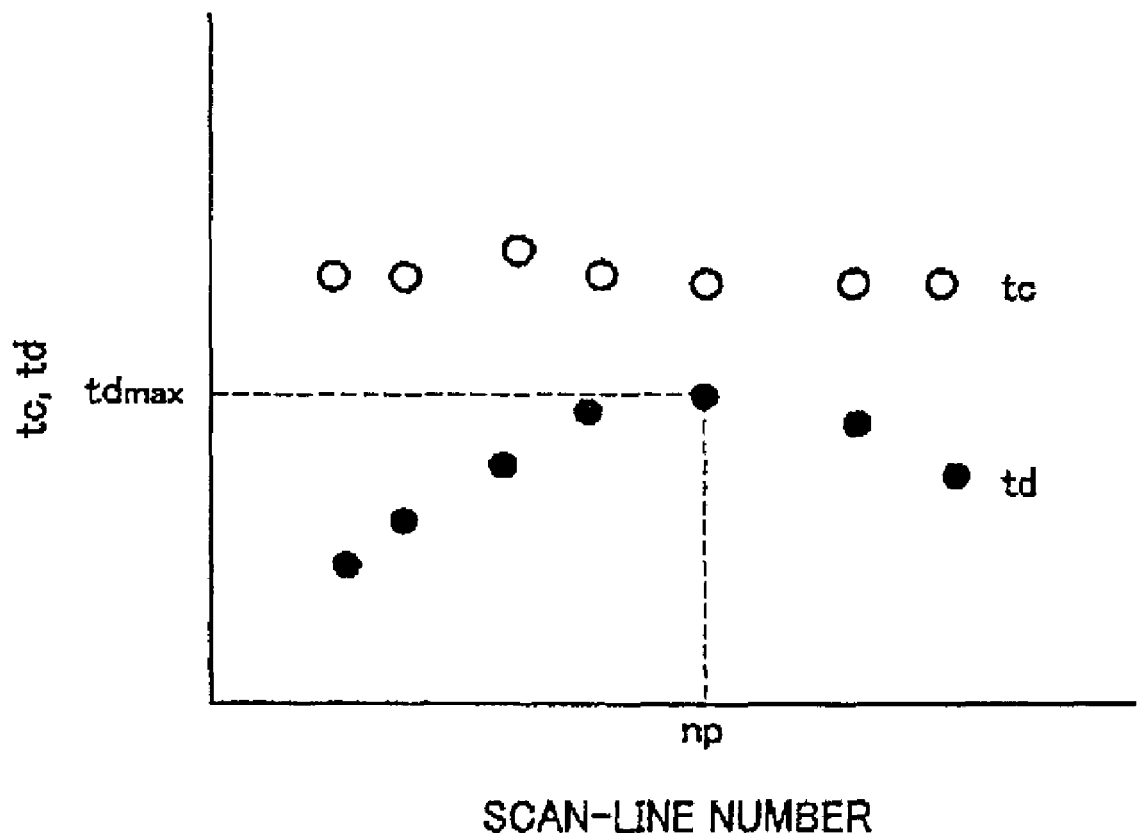
FIG. 9 is a graph for explaining how a time elapsed to and a time difference td change as a scan-line number changes.

In FIG. 9, there is illustrated in graph a relationship between the scan-line number n, the elapsed time tc and the time difference td. As the scan-line number n increases, the time difference td exhibits an upwardly convex distribution pattern, while the elapsed time tc is generally held constant. That is to say, the time difference td changes in a pattern having a maximum value tdmax, and the scan-line number n of one of the scan lines which corresponds to the maximum value tdmax is denoted by np. Once the scan-line number np has been identified, a vertical position of the pupil center C can be determined.

Based on the above findings, if the determination of the step S10 illustrated in FIG. 5 becomes "YES," then, at a step S11, the maximum value tdmax is set to a maximum one of a plurality of time differences td which have been stored in the RAM 216 since the implementation of the step S9. Subsequently, at a step S12, the elapsed time tc is determined as the sum of one-half the maximum value tdmax and the center time point tm1. The determined elapsed time tc indicates a horizontal position of the pupil center C. Following that, at a step S13, the scan-line number np is set to one of the scan-line numbers n which corresponds to the maximum value tdmax. The scan-line number np indicates a vertical position of the pupil center C.

Subsequently, at a step S14, a control amount of the actuator 192 is determined for changing the shape of the variable prism 190 in order to cause the optical axis of the imaging light to follow the position of the pupil center C, based on the elapsed time tc and the scan-line number np obtained at the steps S12 and S13. The control amount is meant to be an amount by which the actuator 192 is required to be controlled The control amount is to be achieved by the actuator 192 for changing the current position of the optical axis of the imaging light so as to become coincident with the pupil center C.

Following that, at a step S15, a signal required for achieving the determined control amount is supplied to the actuator 192 via the driving circuit 194.

Then, one cycle of execution of this optical-axis follow-up control program is terminated.

As will be evident from the above description, in the present embodiment, the IR laser 46, the scanning unit 24, the infrared semi-transparent mirror 170, the lens 172, the photodiode 174, and the pupil-position determining circuit 180 together constitute an example of the "pupil tracking device" constructed according to the above mode (1), and this RSD constitutes an example of the "image display apparatus" constructed according to the above mode (8).

Further, in the present embodiment, the IR laser 46 constitutes an example of the "light emitter" set forth in the above mode (1) and an example of the "tracking-purpose light emitter" set forth in the above mode (8), and the R laser 40, the G laser 42, and the B laser 44 each constitute an example of the "display-purpose light emitter" set forth in the above mode (8).

Still further, in the present embodiment, the infrared light constitutes an example of the "light beam" set forth in the above mode (1) and an example of the "non-visible light beam" set forth in the above mode (8), the imaging light constitutes an example of the "visible light beam" set forth in the above mode (8), and the combining optical system 70, in particular, constitutes an example of the "combiner" set forth in the above mode (8).

Additionally, in the present embodiment, the scanning unit 24 constitutes an example of the "scanner" set forth in the above mode (1) and an example of the "scanner" set forth in the above move (8), the relay optical system 160 constitutes an example of the "guide" set forth in the above mode (8), and the photodiode 174, in particular, constitutes an example of the "detector" set forth in the above mode (1) and an example of the "detector" set forth in the above mode (8).

Still additionally, in the present embodiment, the variable prism 190, in particular, constitutes an example of the "deflector" set forth in the above mode (16), the pupil-position determining circuit 180 combining the computer 210 constitutes an example of the "processor" set forth in the above mode (1) and an example of the "controller" set forth in the above mode (8), and the last-stage lens 164 constitutes an example of the "focus adjuster" set forth in each one of the above modes (10)-(13).

Still yet additionally, in the present embodiment, a portion of the computer 210 which is assigned to implement the steps S1-S12 of the optical-axis follow-up control program depicted in FIG. 5 constitutes an example of the "first position tracker" set forth in the above mode (6), and a portion of the computer 210 which is assigned to implement the steps S1-S11 and S13 of the optical-axis follow-up control program depicted in FIG. 5 constitutes an example of the "second position tracker" set forth in the above mode (7).

It is added that, although, in the present embodiment, the variable prism 190 is employed as an example of the "deflector" set forth in the above mode (16), the variable prism 190 may be replaced with a variable diffractive element.

An example of such a variable diffractive element is an Acousto Optic Deflector (AOD). This AOD, when employed, may be disposed within this RSD at the same position as with the variable prism 190.

It is further added that, in the present embodiment, composite light of the imaging light and the tracking light (e.g., the infrared light) is in the form of a beam having a cross section shaped as a circle, as usual, and therefore, the beam of the composite light is two-dimensionally scanned for forming a two-dimensional image.

Alternatively, in an exemplary modified-version of the present embodiment, the composite light of the imaging light and the tracking light (i.e., at least including the imaging light) is modified with respect to the original version of the present embodiment, to alternative composite light or imaging light in the form of a beam having a cross section shaped as a vertically elongated ellipse. The vertically elongated ellipse is an ellipse having a vertical major or longer axis and a horizontal minor or shorter axis.

In this exemplary modified-version, the minor axis of the ellipse is almost coincident in length with the diameter of the aforementioned circle, while the major axis of the ellipse is longer than the diameter of the circle when the surface of the eye 10 is illuminated with the associated light.

Further, in this exemplary modified-version, for the beam cross-section to be ovalized or flattened, various arrangements may be employed. In one exemplary arrangement, a cylindrical lens is additionally disposed at any position which is located optically upstream of the horizontal scanning system 130 and at which a light beam travels generally as a parallel beam. In an alternative exemplary arrangement, a toroidal lens is additionally disposed at any position which is interposed between the horizontal scanning system 130 and the vertical scanning system 132 and at which a light beam travels generally as a parallel beam.

Accordingly, in this exemplary modified-version, the scanning unit 24 is modified with respect to the original version of the present embodiment, to an alternative scanning unit for scanning the composite light one-dimensionally in a horizontal direction. Similarly, the pupil detector 30 is modified to an alternative pupil detector for detecting an actual position of the pupil 12 one-dimensionally in a horizontal direction. Still similarly, the follow-up controller 32 is modified to an alternative follow-up controller for controlling the optical axis of the composite light one-dimensionally in a horizontal direction.

As a result, in this exemplary modified-version, the alternative pupil detector and the alternative follow-up controller together constitute an example of the "controller" set forth in the above mode (20), the horizontal direction constitutes an example of the "one direction" set forth in the same mode, and the vertically elongated ellipse is an example of the "flattened shape" set forth in the same mode.

It is further added that, although, in the present embodiment, the curvature of wavefront of the imaging light is modulated for forming an image, to thereby alter the depth of a display image, this is not essential in practicing the present invention.

Next, a second embodiment of the present invention will be described.

The present embodiment is common to the first embodiment with respect to many elements, and is different from the first embodiment only with respect to the configuration for shifting the optical axis. Therefore, only the different elements of the present embodiment from those of the first embodiment will be described below in greater detail, while the common elements of the present embodiment to those of the first embodiment will be omitted in detailed description by reference using the identical reference numerals or names.

In the first embodiment, the variable prism 190 enables the direction of the optical axis of the imaging light to be shifted or deflected, to thereby control the entrance position of the imaging light on the eye 10 to match with the position of the pupil 12.

Figure 10:
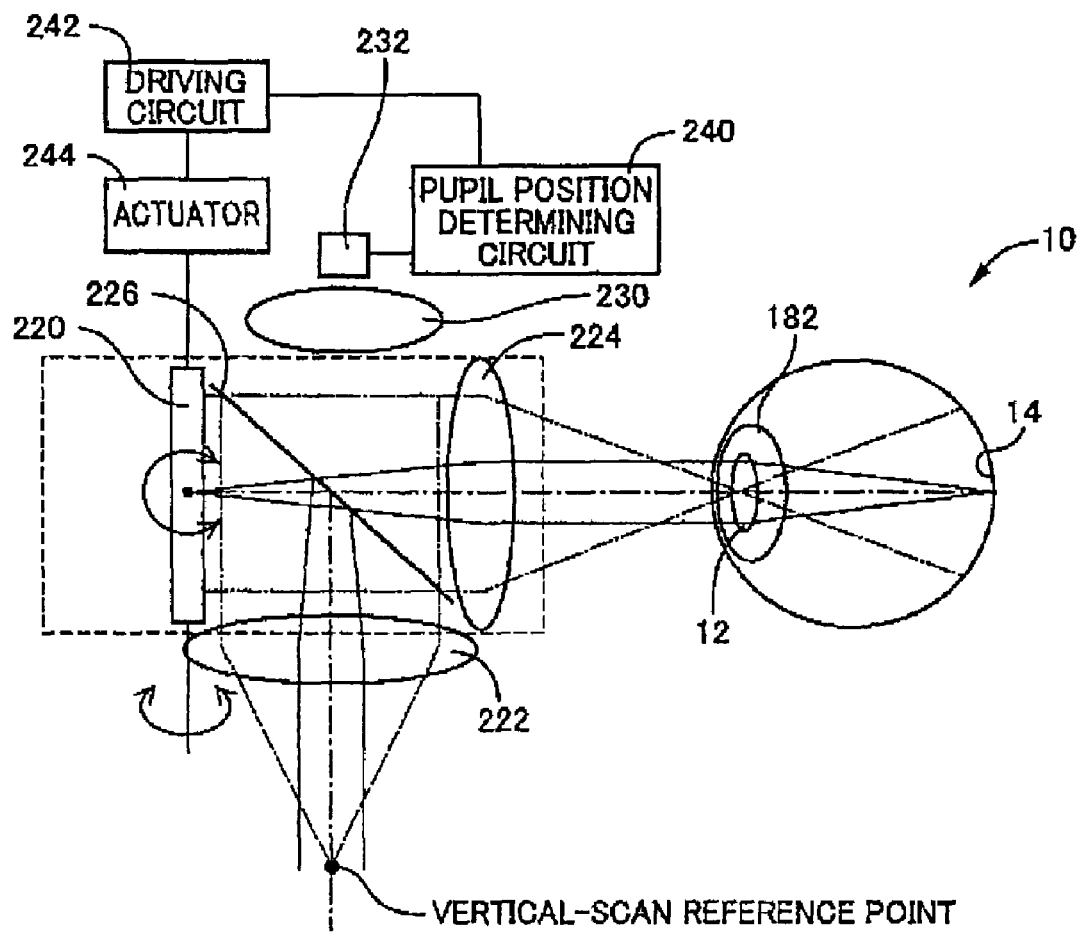
FIG. 10 is an optical path diagram for explaining a principle in which an optical axis is shifted within a retinal scanning display constructed according to a second embodiment of the present invention.

In contrast, in the present embodiment, as illustrated in FIG. 10, for the direction of the optical axis of the imaging light to be shifted, a movable mirror 220 is tilted (is changed in its tilt angle) which is inclined with respect to two axes each perpendicular to the optical axis of the imaging light. An example of the movable mirror 220 is a two-dimensionally-driven and galvanometer-based mirror.

More specifically, as illustrated in FIG. 10, in the present embodiment, a first-stage lens 222 and a last-stage mirror 224 are arrayed relative to each other to have their two orthogonal optical axes A semi-transparent mirror 226 is disposed at a point at which the two optical axes of the first- and the last-stage lens 222, 224 cross each other orthogonally.

The semi-transparent mirror 226 reflects the light coming from the first-stage lens 222, to a direction away from the last-stage lens 224, resulting in entry into the movable mirror 220. The movable mirror 220 has its center position disposed coincident with a focus position of the light coming from the semi-transparent mirror 226.

The movable mirror 220 reflects back the incident light to the semi-transparent mirror 226, and in turn, the semi-transparent mirror 226 causes the incident light to pass through the semi-transparent mirror 226 into the last-stage lens 224 along a straight line.

Once the movable mirror 220 has been tilted about the two orthogonal optical axes through which the center position of the movable mirror 220 passes, the reflected light from the movable mirror 220 is deflected, resulting in a change in the direction of the optical axis of the imaging light.

As illustrated in FIG. 10, in the present embodiment, similarly with the first embodiment, a lens 230 which is an optical element for collecting infrared light reflected from the surface of the eye 10, and a photodiode 232 are disposed on a side opposite to a side of the first-stage lens 222, with respect to the semi-transparent mirror 226. The semi-transparent mirror 226 reflects the light reflected from the surface of the eye 10 toward the lens 230.

As a result, in the present embodiment, the single semi-transparent mirror 226 provides both the function of directing the imaging light and the infrared light from the scanning unit 24 to the movable mirror 220 acting as an optical-axis shifter, and the function of directing the light reflected from the surface of the eye 10 to the photodiode 232.

The photodiode 232 is adapted to supply a signal responsive to the intensity of return light from the eye 10 (i.e., incident light on the photodiode 232) to a pupil-position determining circuit 240. The pupil-position determining circuit 240 is adapted to control the orientation of the movable mirror 220 about two axes, by way of a driving circuit 242 and an actuator 244, based on a supplied signal, in a similar manner to that in the first embodiment. The control allows the optical axis of the imaging light to follow an actual position of the pupil 12, As will be evident from the above explanation, in the present embodiment, the movable mirror 220 constitutes an example of the "deflector" set forth in the above mode (16) and an example of the "oscillating mirror" set forth in the above mode (17).

Next, a third embodiment of the present invention will be described.

The present embodiment is common to the first embodiment with respect to many elements, and is different from the first embodiment only with respect to the configuration for shifting the optical axis of the imaging light. Therefore, only the different elements of the present embodiment from those of the first embodiment will be described below in greater detail, while the common elements of the present embodiment to those of the first embodiment will be omitted in detailed description by reference using the identical reference numerals or names.

In the first embodiment, the variable prism 190 enables the direction of the optical axis of the imaging light to be shifted or deflected, to thereby control the entrance position of the imaging light on the eye 10.

In contrast, in the present embodiment, a movable mirror inclined with respect to the optical axis of the imaging light is translated or shifted parallel, in a direction perpendicular to the optical axis of the imaging light, to thereby translate the optical axis of the imaging light, resulting in a change in the entrance position of the imaging light on the eye 10.

Figure 11:
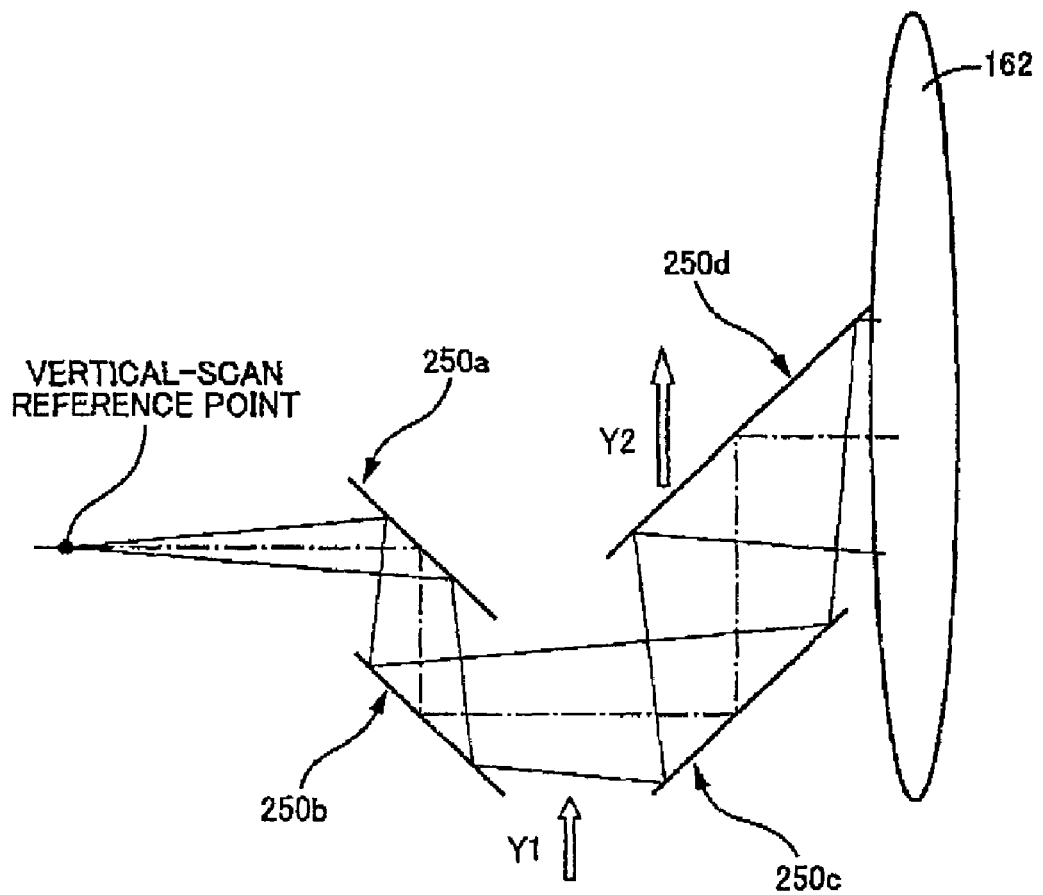
FIG. 11 is an optical path diagram for explaining a principle in which an optical axis is shifted within a retinal scanning display constructed according to a third embodiment of the present invention.

More specifically, as illustrated in FIG. 11, in the present embodiment, first through fourth mirrors 250a, 250b, 250c, and 250d are disposed between the vertical scanning system 132 of the scanning unit 24 and the first-stage lens 162 of the relay optical system 160, so as to achieve an inclination angle of 45.degree. relative to the optical axis of the imaging light. This arrangement causes the optical axes of the imaging light and the infrared light to be bent at an angle of 90. degree., each time the imaging light and the infrared light pass through each of the mirrors 250a, 250b, 250c, and 250d.

The first mirror 250a, which the light coming from the vertical scanning system 132 first enters, is stationary, but the remaining second through fourth mirror 250b, 250c, and 250d which the light subsequently enter are each disposed to allow each mirror 250b, 250c, 250d to translate or move parallel in a direction perpendicular to the optical axis of the imaging light. Once the fourth mirror 250d, which the light finally enters (because the mirror 250d is disposed immediately before the relay optical system 160), has been translated, the entrance position of the imaging light on the eye 10 of the viewer is caused to change.

If the fourth mirror 250d is solely translated, then an undesirable change is made in the optical path length of the imaging light between the vertical scanning system 132 and the first-stage lens 162.

In the present embodiment, for such an undesirable change to be cancelled, the second and third mirrors 250b and 250c, when there is the need to translate the fourth mirror 250d, are translated in the same direction as the fourth mirror 250d, by a movement amount Y1 equal to one-half a required parallel-movement-amount Y2 of the fourth mirror 250d.

As a result, in the present embodiment, the parallel movements of the second through fourth mirrors 250b, 250c, and 250d allow the entrance position of the imaging light on the eye 10 of the viewer, to move without causing any changes in the optical path length of the imaging light.

As will be evident from the above explanation, in the present embodiment, the fourth mirror 250d, in particular, constitutes an example of the "parallel shifter" set forth in the above mode (18) and an example of the "movable mirror" set forth in the above mode (19).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims

What is claimed is:

1. A device for tracking a position of a pupil of an eyeball, by directing light toward the eyeball and using a portion of the light which is reflected from the eyeball, the device comprising:
   a light emitter emitting a light beam;
   a scanner scanning two-dimensionally the light beam emitted from the light emitter, over the eyeball, in a primary scan direction and a secondary scan direction which are oriented crosswise relative to each other, to thereby create a plurality of successive scan lines;
   a detector detecting a time-varying intensity of a reflected instantaneous light beam which is a portion of the light beam entering a surface of the eyeball which is reflected therefrom, and producing an intensity signal indicative of the intensity of the reflected instantaneous light beam; and
   a processor which tracks a pupil position based on intensity changes of the reflected instantaneous light beam represented by the intensity signal outputted from the detector.

2. The device according to claim 1, wherein the intensity of the reflected instantaneous light beam represented by the intensity signal outputted from the detector has first intensity changes dependent on position changes of the light beam along the individual scan lines, and second intensity changes dependent on position changes of the light beam across the scan lines, and
   the processor tracks a two-dimensional pupil position based on the first and second intensity changes of the reflected instantaneous light beam.

3. The device according to claim 1, wherein the light beam is scanned two-dimensionally on a scan region which is located on the surface of the eyeball so as to cover the pupil with an area size larger than that of the pupil.

4. The device according to claim 3, wherein the scanner scans the light beam entering the scanner, to thereby emit scanning light, and
   the emitted scanning light enters the eyeball so as to have a focus position which is located on an optical axis extending between the scanner and a retina of the eyeball, at a predetermined distance from the pupil.

5. The device according to claim 1, wherein the processor, in a presence of two high-level portions of the intensity signal, tracks the pupil position based on the two high-level portions, per scan line, and
   each one of the high-level portions of the intensity signal indicates that the intensity of the reflected instantaneous light beam exceeds a threshold value.

6. The device according to claim 5, wherein the processor includes a first position tracker tracking the pupil position in the primary scan direction, based on a middle position between the two high-level portions of the intensity signal.

7. The device according to claim 5, wherein the processor includes a second position tracker tracking the pupil position in the secondary scan direction, based on a position of one of the plurality of scan lines, the intensity signal of which has the two high-level portions spaced apart from each other by a substantially maximum distance.

8. An apparatus for projecting an image directly onto a retina of a viewer, by directing a visible light beam representing the image toward the retina through a pupil of the viewer, the apparatus comprising:
   a display-purpose light emitter emitting the visible light beam for displaying the image;
   a tracking-purpose light emitter emitting a non-visible light beam toward an eyeball of the viewer, for tracking a pupil position;
   a combiner combining the visible light beam emitted from the display-purpose light emitter and the non-visible light beam emitted from the tracking-purpose light emitter with each other, to thereby produce a composite light beam;
   a scanner scanning the produced composite light beam two-dimensionally, over the eyeball, in a primary scan direction and a secondary scan direction which are oriented crosswise relative to each other, to thereby create a plurality of successive scan lines;
   a guide guiding the scanned composite light beam toward the pupil;
   a detector detecting a time-varying intensity of a reflected light beam which is a portion of the non-visible light beam entering a surface of the eyeball which is reflected therefrom, and producing an intensity signal indicative of the intensity of the reflected light beam; and
   a controller which tracks the pupil position based on intensity changes of the reflected light beam represented by the intensity signal outputted from the detector, and which controls an optical axis along which the visible light beam travels toward the eyeball, so as to follow an actual pupil position, based on the tracked pupil position.

9. The apparatus according to claim 8, wherein the intensity of the reflected light beam represented by the intensity signal outputted from the detector has first intensity changes dependent on position changes of the light beam along the individual scan lines, and second intensity changes dependent on position changes of the light beam across the scan lines, and
   the controller tracks a two-dimensional pupil position based on the first and second intensity changes of the reflected light beam, and controls the optical axis along which the visible light beam travels toward the eyeball, so as to follow the actual pupil position, based on the tracked pupil position.

10. The apparatus according to claim 8, wherein the scanner scans the non-visible light beam entering the scanner, to thereby emit scanning non-visible light,
    the apparatus further comprising a focus adjuster adjusting a focus position of the emitted scanning non-visible light so as to be located on an optical axis extending between the scanner and the retina, at a predetermined distance from the pupil.

11. The apparatus according to claim 10, wherein the focus adjuster is disposed at the guide.

12. The apparatus according to claim 11, wherein the focus adjuster is disposed at an optically downstream part of the guide.

13. The apparatus according to claim 11, wherein the focus adjuster is configured to include at least one of a lens made of a glass material having a wavelength-dependent dispersion characteristic, and a diffractive element.

14. The apparatus according to claim 8, wherein the guide is configured to include a relay optical system.

15. The apparatus according to claim 8, wherein the controller includes optics disposed optically downstream of and away from the scanner.

16. The apparatus according to claim 15, wherein the scanner scans the visible light beam entering the scanner, to thereby emit scanning visible light, and the optics includes a deflector which is disposed at a focus position of the emitted scanning visible light and which deflects the optical axis along which the scanning visible light travels.

17. The apparatus according to claim 16, wherein the deflector is configured to include at least one of a variable prism, an oscillating mirror, and a variable diffraction grating.

18. The apparatus according to claim 15, wherein the scanner scans the visible light beam entering the scanner, to thereby emit scanning visible light, and the optics includes a parallel shifter effecting a parallel shifting of the optical axis along which the emitted scanning visible light travels, in a perpendicular direction to the optical axis.

19. The apparatus according to claim 18, wherein the parallel shifter is configured to include a movable mirror which is inclined with respect to the optical axis and which is to be translated in the perpendicular direction.

20. The apparatus according to claim 8, wherein the controller tracks the pupil position and controls the optical axis in one direction, and the composite light beam is configured to have a cross section with a generally flattened shape extending perpendicular to the one direction.

21. The device according to claim 1, wherein the light beam is scanned over the eyeball across its iris, the intensity changes of the reflected light beam are each caused by a scan of the light beam across the iris, and the intensity signal has level changes caused by the intensity changes of the reflected light beam.

22. The device according to claim 1, wherein the intensity signal is detected in association with a corresponding one of the scan lines, and the processor determines the two-dimensional position of the pupil based on a position of a high-level portion of the intensity signal and a position of the corresponding scan line.

* * * * *